(12) United States Patent  
Wenderow et al.

(10) Patent No.: US 9,402,977 B2  
(45) Date of Patent: *Aug. 2, 2016

(54) CATHETER SYSTEM

(71) Applicant: Corindus, Inc., Waltham, MA (US)

(72) Inventors: Tal Wenderow, Newton, MA (US); Thomas Bromander, Andover, MA (US); James J. Kennedy, III, Deerfield, NH (US); Stanley O. Thompson, New Boston, NH (US); Jon B. Taylor, Groton, MA (US); Jeffrey Lightcap, Plandome, NY (US); John Murphy, North Reading, MA (US)

(73) Assignee: CORINDUS INC., Waltham, MA (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/914,976

(22) Filed: Jun. 11, 2013

(65) Prior Publication Data

US 2014/0058322 A1 Feb. 27, 2014

Related U.S. Application Data

(63) Continuation of application No. 12/626,503, filed as application No. PCT/US2009/042720 on May 4, 2009, now Pat. No. 8,480,618.

(60) Provisional application No. 61/050,933, filed on May 6, 2008.

(51) Int. Cl.
*A61M 25/092* (2006.01)
*A61M 25/01* (2006.01)
*A61B 19/00* (2006.01)

(Continued)

(52) U.S. Cl.
CPC ........ *A61M 25/0147* (2013.01); *A61B 19/2203* (2013.01); *A61B 19/5244* (2013.01); *A61M 25/0113* (2013.01); *A61M 25/09041* (2013.01); *A61B 2017/00477* (2013.01); *A61B 2019/2211* (2013.01); *A61B 2019/448* (2013.01)

(58) Field of Classification Search
CPC ............ A61M 25/0136; A61M 25/09; A61M 25/09041; A61B 1/00133
See application file for complete search history.

(56) References Cited

U.S. PATENT DOCUMENTS

| 2,718,598 A | 9/1955 | Graf |
| 3,147,953 A | 9/1964 | Arth |

(Continued)

FOREIGN PATENT DOCUMENTS

| DE | 2856439 A | 7/1980 |
| DE | 4233323 A | 4/1994 |

(Continued)

OTHER PUBLICATIONS

U.S. Appl. No. 29/378,948, filed Nov. 11, 2010, Murphy.

(Continued)

*Primary Examiner* — Laura Bouchelle
(74) *Attorney, Agent, or Firm* — Rathe Lindenbaum LLP

(57) ABSTRACT

A robotic catheter system is provided. The robotic catheter system includes a housing and a drive assembly coupled to the housing. The drive assembly is configured to impart movement to a catheter device. The catheter system includes a release structure permitting the drive assembly to be decoupled and removed from the housing without removing the catheter device from a patient.

19 Claims, 25 Drawing Sheets

(51) Int. Cl.
*A61M 25/09* (2006.01)
*A61B 17/00* (2006.01)

(56) References Cited

U.S. PATENT DOCUMENTS

| | | |
|---|---|---|
| 3,308,297 A | 3/1967 | Mansker |
| 4,254,341 A | 3/1981 | Herr et al. |
| 4,382,184 A | 5/1983 | Wernikoff |
| 4,581,538 A | 4/1986 | Lenhart |
| 4,965,456 A | 10/1990 | Huettenrauch et al. |
| 4,977,588 A | 12/1990 | Van der Ende |
| 5,015,864 A | 5/1991 | Maleki |
| 5,049,147 A | 9/1991 | Danon |
| 5,090,044 A | 2/1992 | Kobayashi |
| 5,133,364 A | 7/1992 | Palermo et al. |
| 5,139,473 A | 8/1992 | Bradshaw et al. |
| 5,185,778 A | 2/1993 | Magram |
| 5,217,474 A | 6/1993 | Zacca et al. |
| 5,318,541 A | 6/1994 | Viera et al. |
| 5,351,676 A | 10/1994 | Putman |
| 5,377,678 A | 1/1995 | Dumoulin et al. |
| 5,396,880 A | 3/1995 | Kagan et al. |
| 5,423,321 A | 6/1995 | Fontenot |
| 5,425,382 A | 6/1995 | Golden et al. |
| 5,434,775 A | 7/1995 | Sims et al. |
| 5,464,023 A | 11/1995 | Viera |
| 5,484,407 A | 1/1996 | Osypka |
| 5,487,734 A | 1/1996 | Thorne et al. |
| 5,492,131 A | 2/1996 | Galel |
| 5,524,180 A | 6/1996 | Wang et al. |
| 5,540,649 A | 7/1996 | Bonnell et al. |
| 5,578,014 A | 11/1996 | Erez et al. |
| 5,584,078 A | 12/1996 | Saboory |
| 5,586,968 A | 12/1996 | Gruendl et al. |
| 5,623,943 A | 4/1997 | Hackett et al. |
| 5,644,613 A | 7/1997 | Mick |
| 5,654,864 A | 8/1997 | Ritter et al. |
| 5,690,645 A | 11/1997 | Van Erp |
| 5,697,377 A | 12/1997 | Wittkampf |
| 5,704,897 A | 1/1998 | Truppe |
| 5,706,827 A | 1/1998 | Ehr et al. |
| 5,728,044 A | 3/1998 | Shan |
| 5,741,271 A | 4/1998 | Nakao et al. |
| 5,779,623 A | 7/1998 | Bonnell |
| 5,821,920 A | 10/1998 | Rosenberg et al. |
| 5,842,987 A | 12/1998 | Sahadevan |
| 5,851,182 A | 12/1998 | Sahadevan |
| 5,882,333 A | 3/1999 | Schaer et al. |
| 5,957,941 A | 9/1999 | Ream |
| 5,981,964 A | 11/1999 | McAuley et al. |
| 6,004,276 A | 12/1999 | Wright et al. |
| 6,013,038 A | 1/2000 | Pflueger |
| 6,024,749 A | 2/2000 | Shturman et al. |
| 6,048,300 A | 4/2000 | Thornton et al. |
| 6,083,170 A | 7/2000 | Ben-Haim |
| 6,096,004 A | 8/2000 | Meglan et al. |
| 6,126,647 A | 10/2000 | Posey et al. |
| 6,171,234 B1 | 1/2001 | White et al. |
| 6,233,476 B1 | 5/2001 | Strommer et al. |
| 6,258,052 B1 | 7/2001 | Milo |
| 6,261,247 B1 | 7/2001 | Ishikawa et al. |
| 6,266,552 B1 | 7/2001 | Slettenmark |
| 6,285,898 B1 | 9/2001 | Ben-Haim |
| 6,290,675 B1 | 9/2001 | Vujanic et al. |
| 6,351,513 B1 | 2/2002 | Bani-Hashemi et al. |
| 6,358,199 B1 | 3/2002 | Pauker et al. |
| 6,375,471 B1 | 4/2002 | Wendlandt et al. |
| 6,447,504 B1 | 9/2002 | Ben-Haim et al. |
| 6,448,571 B1 | 9/2002 | Goldstein |
| 6,497,444 B1 | 12/2002 | Simon |
| 6,499,163 B1 | 12/2002 | Stensby |
| 6,522,909 B1 | 2/2003 | Garibaldi et al. |
| 6,540,670 B1 | 4/2003 | Hirata et al. |
| 6,554,472 B1 | 4/2003 | Dietz et al. |
| 6,610,007 B2 | 8/2003 | Belson et al. |
| 6,653,648 B2 | 11/2003 | Goldstein |
| 6,705,990 B1 | 3/2004 | Gallant et al. |
| 6,726,675 B1 | 4/2004 | Beyar |
| 6,740,103 B2 | 5/2004 | Hall et al. |
| 6,770,066 B1 | 8/2004 | Weaver et al. |
| 6,835,173 B2 | 12/2004 | Couvillon, Jr. |
| 6,878,106 B1 | 4/2005 | Herrmann |
| 6,997,870 B2 | 2/2006 | Couvillon, Jr. |
| 7,087,013 B2 | 8/2006 | Belson et al. |
| 7,112,811 B2 | 9/2006 | Lemer |
| 7,276,044 B2 | 10/2007 | Ferry et al. |
| 7,294,135 B2 | 11/2007 | Stephens et al. |
| D571,912 S | 6/2008 | Ranalletta et al. |
| 7,608,847 B2 | 10/2009 | Rees |
| 7,615,032 B2 | 11/2009 | Whittaker et al. |
| 7,615,042 B2 | 11/2009 | Beyar et al. |
| 7,632,265 B2 | 12/2009 | Hauck et al. |
| 7,663,128 B2 | 2/2010 | Arterson |
| 7,666,135 B2 | 2/2010 | Couvillon, Jr. |
| 7,674,270 B2 | 3/2010 | Layer |
| 7,686,816 B2 | 3/2010 | Belef et al. |
| 7,697,972 B2 | 4/2010 | Verard et al. |
| 7,706,894 B2 | 4/2010 | Stewart et al. |
| 7,729,743 B2 | 6/2010 | Sabczynski et al. |
| 7,766,894 B2 | 8/2010 | Weitzner et al. |
| 7,769,427 B2 | 8/2010 | Shachar |
| D626,250 S | 10/2010 | Wenderow et al. |
| 7,811,294 B2 | 10/2010 | Strommer et al. |
| 7,848,788 B2 | 12/2010 | Tulley et al. |
| 7,887,549 B2 | 2/2011 | Wenderow et al. |
| 7,905,853 B2 | 3/2011 | Chapman et al. |
| 7,967,773 B2 | 6/2011 | Amborn et al. |
| 7,984,659 B2 | 7/2011 | Fujimoto et al. |
| 8,043,362 B2 | 10/2011 | Gong et al. |
| 8,046,049 B2 | 10/2011 | Govari et al. |
| 8,187,229 B2 | 5/2012 | Weitzner et al. |
| 8,231,610 B2 | 7/2012 | Jo et al. |
| 8,257,302 B2 | 9/2012 | Beyar et al. |
| 8,343,096 B2 | 1/2013 | Kirschenman et al. |
| 8,390,438 B2 | 3/2013 | Olson et al. |
| 8,480,618 B2 * | 7/2013 | Wenderow et al. ........ 604/95.01 |
| 8,616,431 B2 | 12/2013 | Timm et al. |
| 2001/0025142 A1 | 9/2001 | Wessels et al. |
| 2002/0087166 A1 | 7/2002 | Brock et al. |
| 2002/0109107 A1 | 8/2002 | Goldstein |
| 2002/0115931 A1 | 8/2002 | Strauss et al. |
| 2002/0168618 A1 | 11/2002 | Anderson et al. |
| 2002/0177789 A1 | 11/2002 | Ferry et al. |
| 2003/0036712 A1 | 2/2003 | Heh et al. |
| 2003/0040671 A1 | 2/2003 | Somogyi et al. |
| 2003/0069719 A1 | 4/2003 | Cunningham et al. |
| 2003/0078003 A1 | 4/2003 | Hunter et al. |
| 2003/0088209 A1 | 5/2003 | Chiu et al. |
| 2003/0176770 A1 | 9/2003 | Merril et al. |
| 2003/0199848 A1 | 10/2003 | Ledesma et al. |
| 2003/0210259 A1 | 11/2003 | Liu et al. |
| 2004/0015974 A1 | 1/2004 | Jeyaraman |
| 2004/0044279 A1 | 3/2004 | Lewin et al. |
| 2004/0064086 A1 | 4/2004 | Gottlieb et al. |
| 2004/0068173 A1 | 4/2004 | Viswanathan |
| 2004/0085294 A1 | 5/2004 | Michelitsch et al. |
| 2004/0113498 A1 | 6/2004 | Kroenke |
| 2004/0138548 A1 | 7/2004 | Strommer et al. |
| 2004/0152974 A1 | 8/2004 | Solomon |
| 2004/0254566 A1 | 12/2004 | Plicchi et al. |
| 2005/0008210 A1 | 1/2005 | Evron et al. |
| 2005/0107697 A1 | 5/2005 | Berke |
| 2005/0119615 A1 | 6/2005 | Noriega et al. |
| 2005/0203382 A1 | 9/2005 | Govari et al. |
| 2005/0222554 A1 | 10/2005 | Wallace et al. |
| 2005/0245846 A1 | 11/2005 | Casey |
| 2005/0256504 A1 | 11/2005 | Long et al. |
| 2005/0273199 A1 | 12/2005 | Ban et al. |
| 2005/0277851 A1 | 12/2005 | Whittaker et al. |
| 2005/0283075 A1 | 12/2005 | Ma et al. |
| 2006/0041181 A1 | 2/2006 | Viswanathan et al. |
| 2006/0041245 A1 | 2/2006 | Ferry et al. |
| 2006/0066574 A1 | 3/2006 | Kim et al. |
| 2006/0074442 A1 | 4/2006 | Noriega et al. |

(56) References Cited

U.S. PATENT DOCUMENTS

| | | | |
|---|---|---|---|
| 2006/0084911 A1* | 4/2006 | Belef et al. ............... | 604/95.01 |
| 2006/0116575 A1 | 6/2006 | Willis | |
| 2006/0146010 A1 | 7/2006 | Schneider | |
| 2006/0186061 A1 | 8/2006 | Briggs et al. | |
| 2006/0229587 A1 | 10/2006 | Beyar et al. | |
| 2006/0258935 A1 | 11/2006 | Pile-Spellman et al. | |
| 2006/0282140 A1 | 12/2006 | Schock et al. | |
| 2007/0016029 A1 | 1/2007 | Donaldson et al. | |
| 2007/0043338 A1 | 2/2007 | Moll et al. | |
| 2007/0060879 A1 | 3/2007 | Weitzner et al. | |
| 2007/0083193 A1 | 4/2007 | Werneth et al. | |
| 2007/0103437 A1 | 5/2007 | Rosenberg | |
| 2007/0106247 A1 | 5/2007 | Burnett et al. | |
| 2007/0118079 A1 | 5/2007 | Moberg et al. | |
| 2007/0123070 A1 | 5/2007 | Bencteux | |
| 2007/0142749 A1 | 6/2007 | Khatib et al. | |
| 2007/0149946 A1 | 6/2007 | Viswanathan et al. | |
| 2007/0185480 A1 | 8/2007 | El-Galley et al. | |
| 2007/0185486 A1 | 8/2007 | Hauck et al. | |
| 2007/0195927 A1 | 8/2007 | Fung et al. | |
| 2007/0197896 A1 | 8/2007 | Moll et al. | |
| 2007/0239106 A1 | 10/2007 | Weitzner et al. | |
| 2007/0250097 A1 | 10/2007 | Weitzner et al. | |
| 2007/0276216 A1 | 11/2007 | Beyar et al. | |
| 2007/0276234 A1 | 11/2007 | Shahidi | |
| 2008/0000485 A1 | 1/2008 | Williams et al. | |
| 2008/0027313 A1 | 1/2008 | Shachar | |
| 2008/0051820 A1 | 2/2008 | Gong et al. | |
| 2008/0059598 A1 | 3/2008 | Garibaldi et al. | |
| 2008/0097224 A1 | 4/2008 | Murphy et al. | |
| 2008/0118023 A1 | 5/2008 | Besson | |
| 2008/0146922 A1 | 6/2008 | Steins et al. | |
| 2008/0161801 A1 | 7/2008 | Steinke et al. | |
| 2008/0167750 A1 | 7/2008 | Stahler et al. | |
| 2008/0217564 A1 | 9/2008 | Beyar et al. | |
| 2008/0221922 A1 | 9/2008 | Putnam et al. | |
| 2008/0221992 A1 | 9/2008 | Bernstein | |
| 2008/0249536 A1 | 10/2008 | Stahler et al. | |
| 2008/0269663 A1 | 10/2008 | Arnold et al. | |
| 2009/0012533 A1 | 1/2009 | Barbagli et al. | |
| 2009/0105639 A1 | 4/2009 | Weitzner et al. | |
| 2009/0110152 A1 | 4/2009 | Manzke et al. | |
| 2009/0131955 A1 | 5/2009 | Wenderow et al. | |
| 2009/0137952 A1 | 5/2009 | Ramamurthy et al. | |
| 2009/0138025 A1 | 5/2009 | Stahler et al. | |
| 2009/0221958 A1 | 9/2009 | Beyar et al. | |
| 2009/0247933 A1 | 10/2009 | Maor et al. | |
| 2009/0247944 A1 | 10/2009 | Kirschenman et al. | |
| 2010/0069833 A1 | 3/2010 | Wenderow et al. | |
| 2010/0073150 A1 | 3/2010 | Olson et al. | |
| 2010/0076308 A1 | 3/2010 | Wenderow et al. | |
| 2010/0076309 A1 | 3/2010 | Wenderow et al. | |
| 2010/0076310 A1 | 3/2010 | Wenderow et al. | |
| 2010/0084586 A1 | 4/2010 | Teodorescu | |
| 2010/0130987 A1 | 5/2010 | Wenderow et al. | |
| 2010/0175701 A1 | 7/2010 | Reis et al. | |
| 2010/0272238 A1 | 10/2010 | Machan et al. | |
| 2010/0292651 A1 | 11/2010 | Yodfat et al. | |
| 2010/0318100 A1 | 12/2010 | Okamoto et al. | |
| 2011/0004144 A1 | 1/2011 | Beiriger et al. | |
| 2011/0015569 A1 | 1/2011 | Kirschenman et al. | |
| 2011/0109283 A1 | 5/2011 | Kapels et al. | |
| 2011/0144658 A1 | 6/2011 | Wenderow et al. | |
| 2011/0152882 A1 | 6/2011 | Wenderow et al. | |
| 2012/0179032 A1 | 7/2012 | Bromander et al. | |

FOREIGN PATENT DOCUMENTS

| | | | |
|---|---|---|---|
| EP | 0329492 | A | 8/1989 |
| EP | 0331944 | A | 9/1989 |
| EP | 0554986 | A | 8/1993 |
| EP | 0590268 | A | 4/1994 |
| EP | 0970663 | A | 1/2000 |
| EP | 1415660 | A | 5/2004 |
| EP | 1442720 | A1 | 8/2004 |
| EP | 1504713 | A | 2/2005 |
| EP | 1554986 | A | 7/2005 |
| EP | 1792638 | A | 6/2007 |
| FR | 2167098 | A | 8/1973 |
| JP | 07184923 | | 7/1995 |
| JP | 7328016 | | 12/1995 |
| SU | 279814 | A | 7/1975 |
| SU | 992067 | A | 1/1983 |
| WO | 9320876 | A | 10/1993 |
| WO | 9426177 | A1 | 11/1994 |
| WO | 9502233 | A | 1/1995 |
| WO | 9621486 | A | 7/1996 |
| WO | 0174252 | A | 10/2001 |
| WO | 0209571 | A | 2/2002 |
| WO | 02064011 | A | 8/2002 |
| WO | 2005000105 | A | 1/2005 |
| WO | 2005117688 | A2 | 12/2005 |
| WO | 2006018841 | A | 2/2006 |
| WO | 2006120666 | A | 11/2006 |
| WO | 2007036925 | A | 4/2007 |
| WO | 2007088208 | A1 | 8/2007 |
| WO | 2009137410 | A1 | 11/2009 |
| WO | 2010025336 | A | 3/2010 |
| WO | 2010025338 | A1 | 3/2010 |
| WO | 2010068783 | A | 6/2010 |
| WO | 2010107916 | A | 9/2010 |
| WO | 2011046874 | A | 4/2011 |

OTHER PUBLICATIONS

Anderson, J., Chui, C.K., Cai. Y., Wang Y., Eng, Z.L.M., Eng, X.M. M., Nowinski, W., Solaiyappan, M., Murphy, K., Gailloud, P. & Venbrux, A., Virtual Reality Training in International Radiology: The John Hopkins and Kent Ridge Digital Labratory Experience, Theime Medical Publishers, 2002, 2 pages, vol. 19, No. 2, New York, NY.

Becker, Y, Cancer in ataxia-telangiectasia patients: Analysis of factors leading to radiation-induced and spontaneous tumors, Anticancer Res., 1986, vol. 6, No. 5, Abstract, pp. 1021-1032, Israel.

Beyar, R., Gruberg, L., Deleanu, D., Roguin, A., Almagor, Y., Cohen, S., Kumar, G., & Wenderow, T., Remote Control Percutaneous Coronary Interventions, Journal of American College of Cardiology, 2006, vol. 47, No. 2, 5 pages, Elsevier Inc., Haifa, Israel.

Biazzi, L. & Garbagna, P., Exposition Aux Radiations Et Protection Pendant Les Examens Angiographiques, Ann. Radiol., 1979, vol. 22, No. 4, Abstract, pp. 345-347, France.

Essinger A., Raimondi, S. & Valley, J.F., Radiation Exposure to the Examiner During Coronary Angiography, Ann. Radiol., 1979 vol. 22 No. 4 Abstract, pp. 340-343, France.

European Search Report for EP Application 14187176.4; mail date Dec. 3, 2014, 5 pages.

Favaretti, C., Stritoni, P., Mariotti, A., Bressan, M. & Razzolini, R., The Distribution and Activities of Hemodynamic Laboratories in Italy: The implications for the Quality of Services, G Ital Cardiol, May 1994, vol. 24 No. 5, Abstract, pp. 477-482, Italy.

Magnavita, N. & Fileni, A., Occupational risk caused by ultrasound in medicine, Radiologica Medica, Jul.-Aug. 1994, vol. 88, No. 1-2, Abstract, pp. 107-111, Italy.

Roach, H., Larson, E., Cobran, T. & Bartlett, B., Intravenous site care practices in critical care: a national survey, Heart Lung, Sep.-Oct. 1995, vol. 24, No. 5, Abstract, pp. 420-424, Washington D.C., United States.

Van Den Brand, M., Utilization or coronary angioplasty and cost or angioplasty disposables in 14 western European countries, Europe Heart Journal, Mar. 1993, vol. 14, No. 3, Abstract, pp. 391-397, Rotterdam, Netherlands.

Wu, J.R., Huang, T.Y., Wu, D.K., Hsu, P.C. & Weng, P.S., An investigation of radiation exposure on pediatric patients and doctors during cardiac catheterization and cineangiography, Journal of Medical Sciences, Sep. 1991, vol. 7, No. 9, Abstract, pp. 448-453, Taiwan, China.

\* cited by examiner

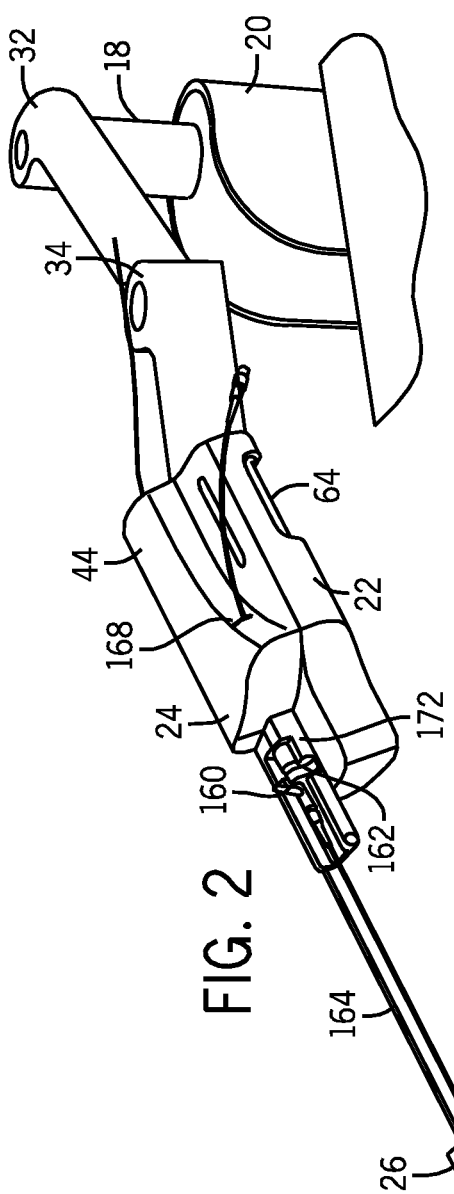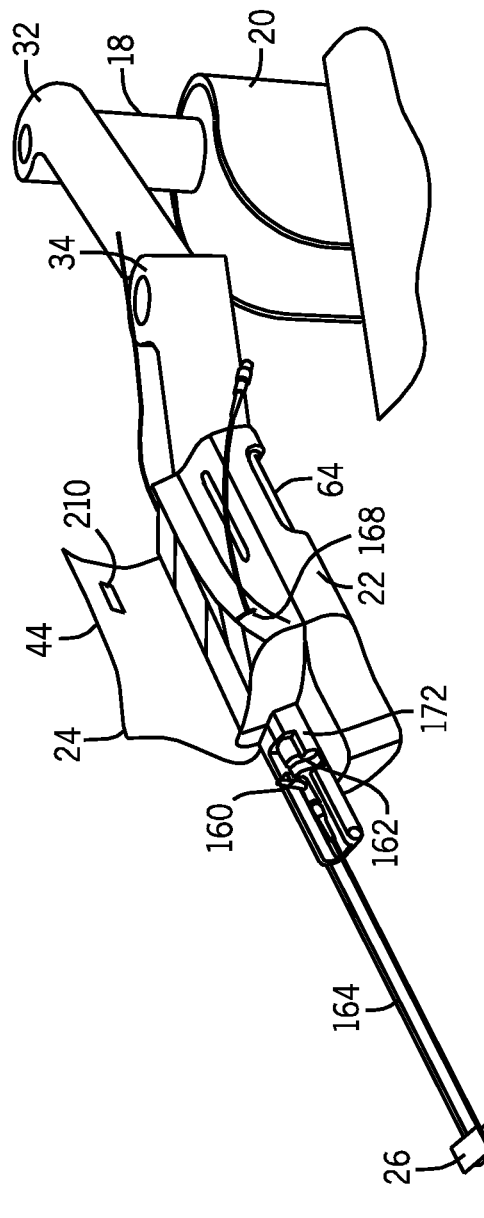

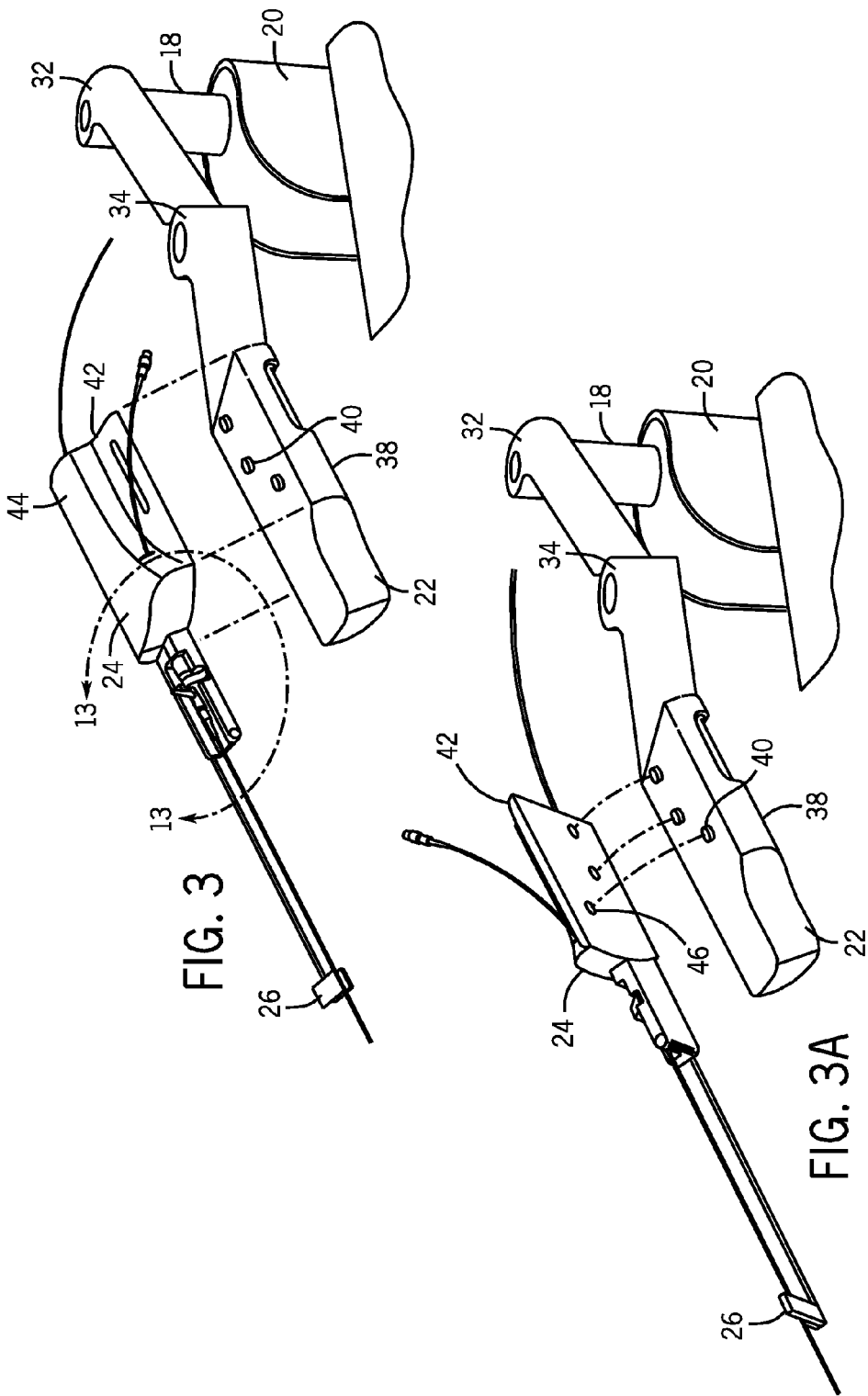

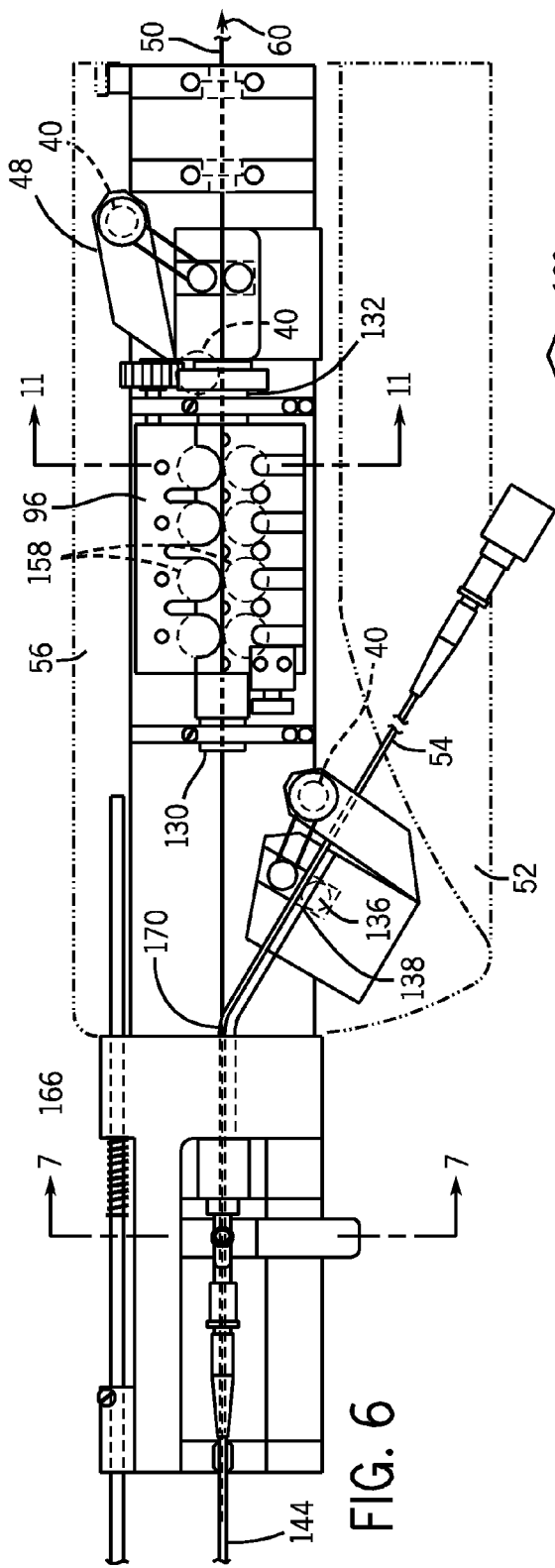

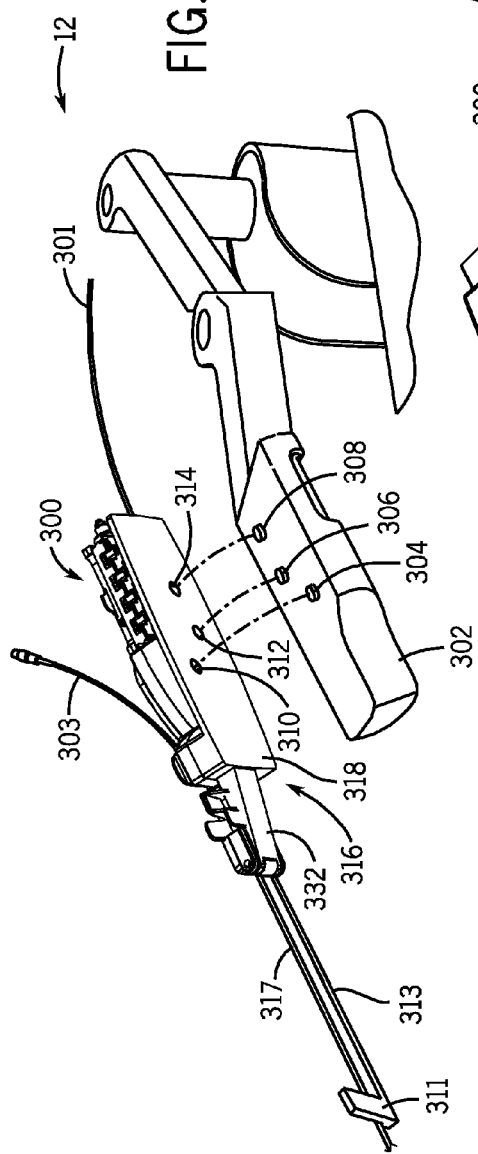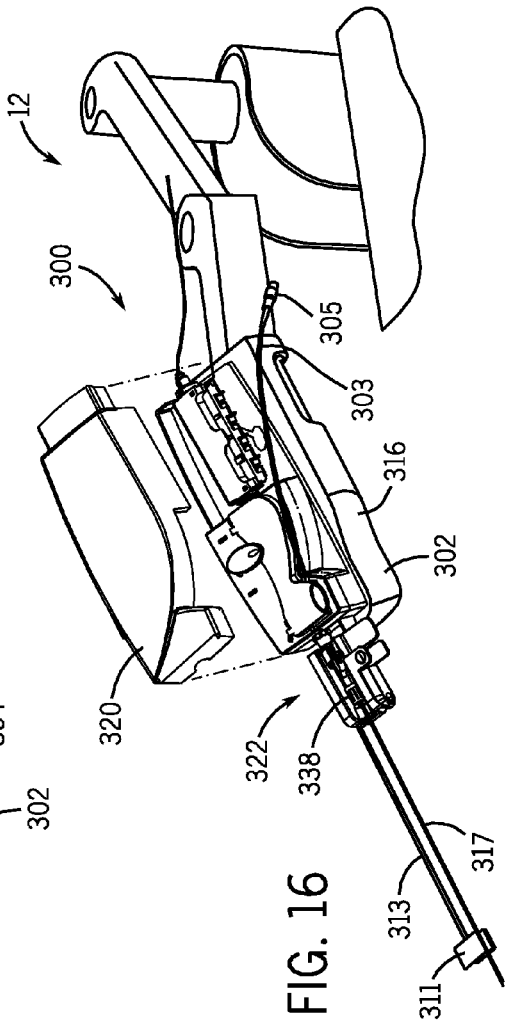

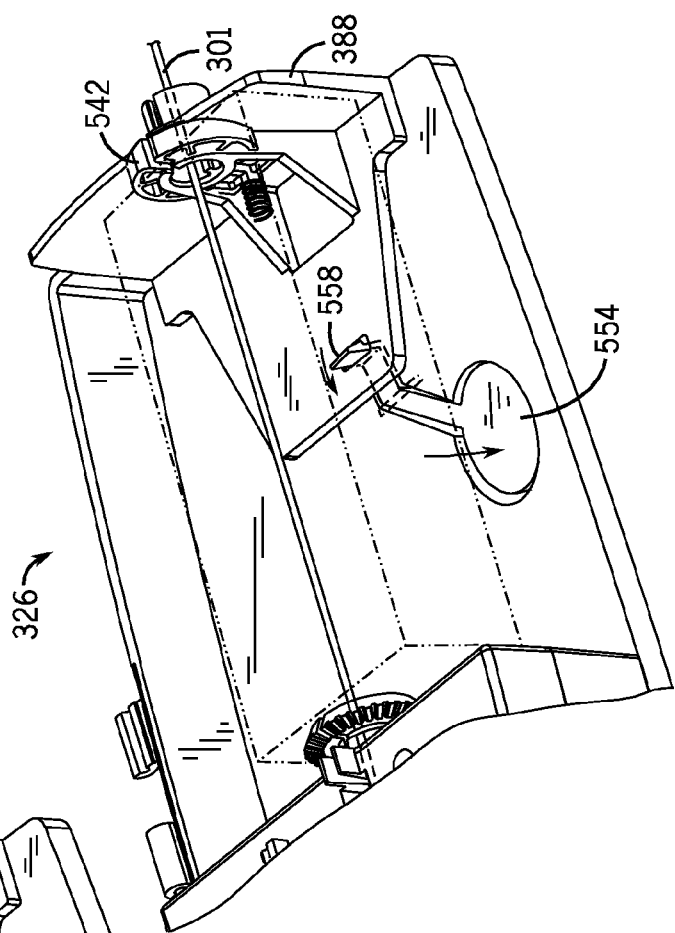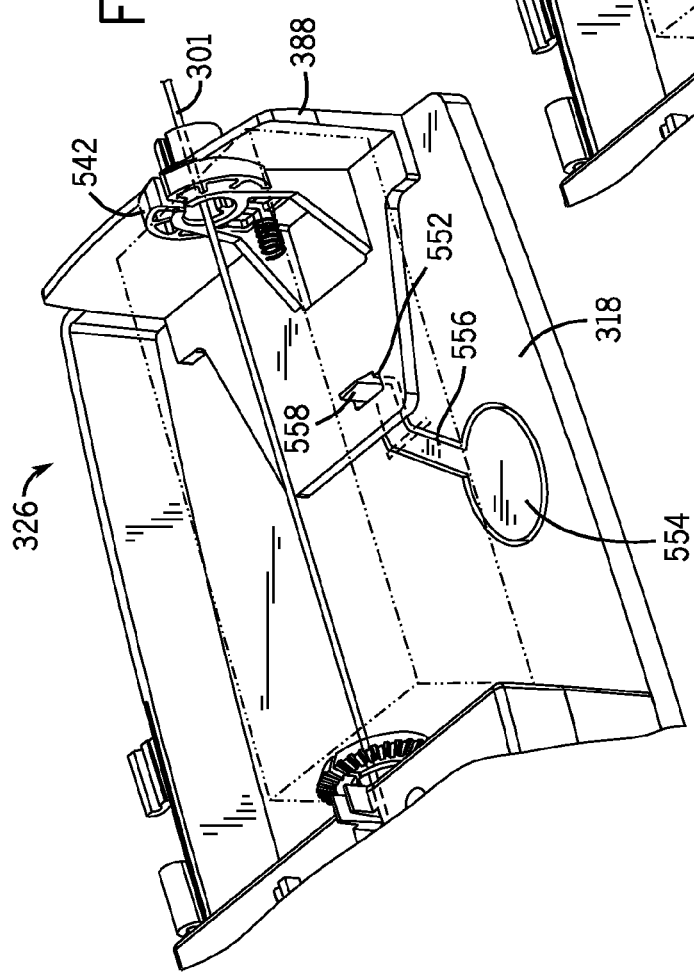

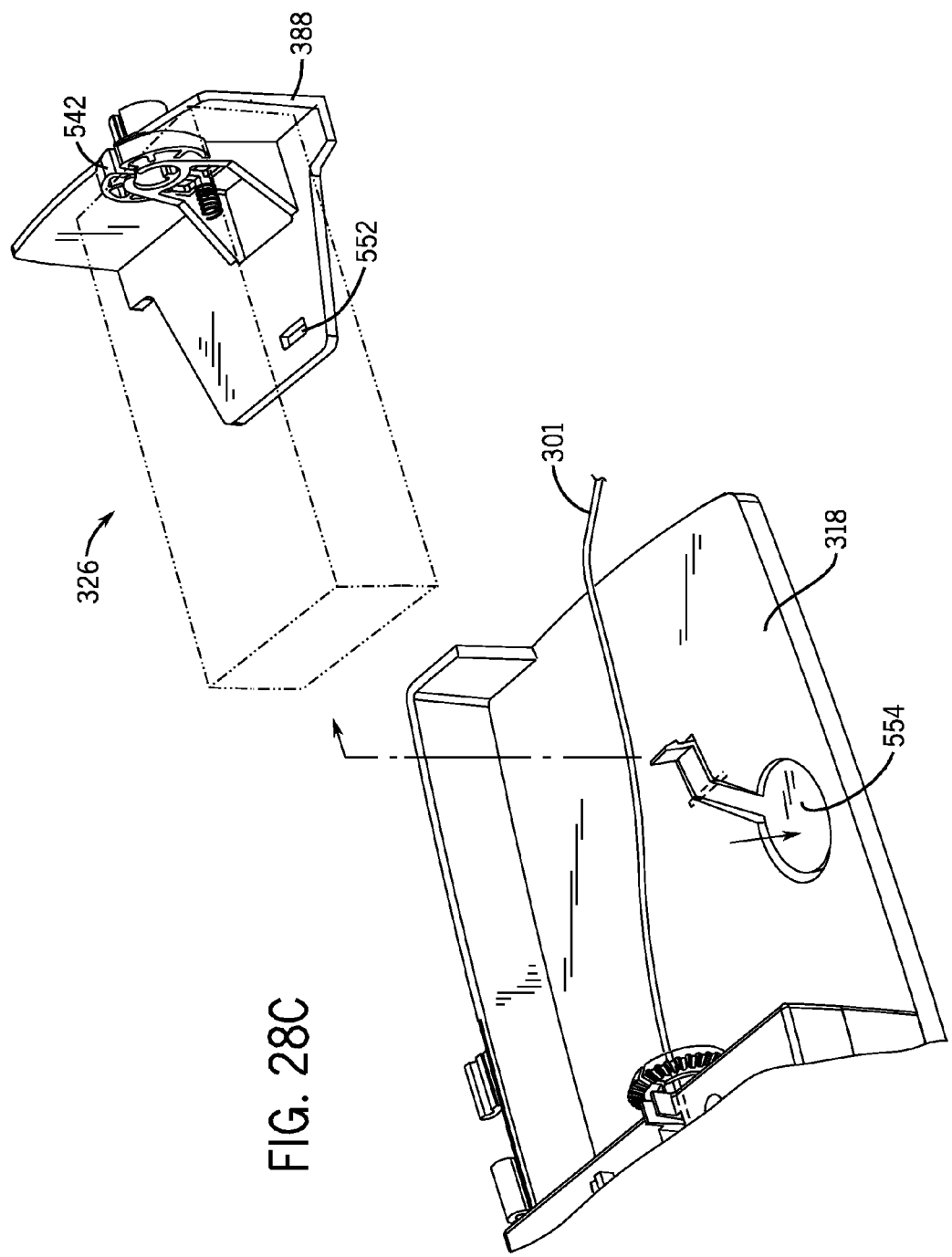

CATHETER SYSTEM

CROSS-REFERENCE TO RELATED PATENT APPLICATIONS

This application is a continuation of U.S. Non Provisional application Ser. No. 12/626,503, filed Nov. 25, 2009, which is a continuation of International Application No. PCT/US09/042,720, filed May 4, 2009, which claims the benefit of U.S. Provisional Application No. 61/050,933, filed May 6, 2008, of which are incorporated herein by reference in their entireties.

BACKGROUND OF THE INVENTION

The present invention relates generally to the field of robotic catheter systems for performing interventional procedures. One interventional procedure used to treat patients with diseased, often obstructed, heart arteries, is a percutaneous coronary intervention ("PCI").

Before performing an interventional procedure with the disclosed invention, a diagnostic procedure is typically performed. An exemplary diagnostic procedure performed before performing a PCI may include a number of steps. Starting in the femoral artery, a 0.038 guide wire is run over the top of the aortic arch. A diagnostic catheter is advanced over the 0.038 guide wire after which the 0.038 guide wire is removed allowing the diagnostic catheter (DC) to return to its preformed shape enabling the DC to access either the left or the right ostium of the aorta. A contrast media is injected through the DC and the heart is x-rayed to identify the existence and location of any lesion. A y-connector may be secured to the end of the DC outside of the patient. The y-connector provides a means for introducing the contrast media or medication. The y-connector employs a one way valve both at the y-connector leg and the free open end. The 0.038 guide is then reinserted into the DC advanced over the top of the aortic arch, and the diagnostic catheter is removed. When the diagnostic is completed the 0.038 guide wire may be left in place for use in a PCI procedure.

SUMMARY OF THE INVENTION

One embodiment of the present invention relates to a robotic catheter system. The robotic catheter system includes a housing and a drive assembly coupled to the housing. The drive assembly is configured to impart movement to a catheter device. The catheter system includes a release structure permitting the drive assembly to be decoupled and removed from the housing without removing the catheter device from a patient.

Another embodiment of the present invention relates to a cassette for use with a robotic catheter system. The cassette includes a housing, an axial drive assembly supported by the housing configured to impart axial movement to a guide wire and a rotational drive assembly coupled to the housing configured to impart rotational movement to the guide wire. The cassette includes a journal removably coupled to the housing and coupled to the rotational drive mechanism such that the rotational drive assembly is permitted to rotate relative to the journal. The cassette includes a mechanical release structure releasably engaging the journal allowing the journal to be decoupled from the housing and permitting the rotational drive assembly to be removed from the housing without removing the guide wire from a patient.

Another embodiment of the present invention relates to a cassette for use with a robotic catheter system configured to couple to a base. The cassette includes a housing having a base plate. The cassette includes a first axial drive mechanism supported by the housing to releasably engage and drive a guide wire along a longitudinal axis of the guide wire and a second axial drive mechanism supported by the housing to releasably engage and drive a working catheter along a longitudinal axis of the working catheter. The cassette includes a rotational drive mechanism supported by the housing to rotate the guide wire about its longitudinal axis and a journal coupled to the rotational drive mechanism and removably coupled to the housing. The journal includes a first portion, a second portion, and a slot positioned in the first portion. The first portion is positioned generally perpendicular to the second portion and is in contact with and generally parallel to the base plate of the housing when the rotational drive mechanism is coupled to the housing. The cassette includes a projection extending from the base plate that releasably engages the slot in the journal to couple the journal to the housing. The cassette includes a button that causes the projection to disengage from the slot when the button is pressed allowing the journal to be decoupled from the housing allowing the rotational drive mechanism to be moved over the proximal end of the guide wire after the journal is decoupled from the housing.

BRIEF DESCRIPTION OF THE DRAWINGS

FIG. 2 is a perspective view of the bedside system.

FIG. 2A is the bedside system of FIG. 2 with the cassette lid in an open position.

FIG. 3 is a perspective view of the bedside system with the cassette removed from the motor drive base.

FIG. 3A is a perspective view of the bottom of the cassette removed from the motor drive base.

FIG. 6 is a top view of the cassette.

FIG. 7 is a cross section of the cassette when the y-connector is secure taken generally along line 7-7.

FIG. 8 is a cross section of the cassette as shown in FIG. 7 when the y-connector is released.

FIG. 15 is a perspective view of a bedside system showing another embodiment of a cassette prior to being attached to the motor drive base.

FIG. 16 is a perspective view of a bedside system showing the cassette of FIG. 15 following attachment to the motor drive base.

FIG. 28A shows a rotational drive assembly coupled to a base plate of a cassette.

FIG. 28B shows depression of a release button to disconnect the rotational drive assembly from the base plate of the cassette.

FIG. 28C shows removal of the rotational drive assembly from the base plate of the cassette leaving the guide wire in place.

DETAILED DESCRIPTION OF THE PREFERRED EMBODIMENTS

Figure 1:
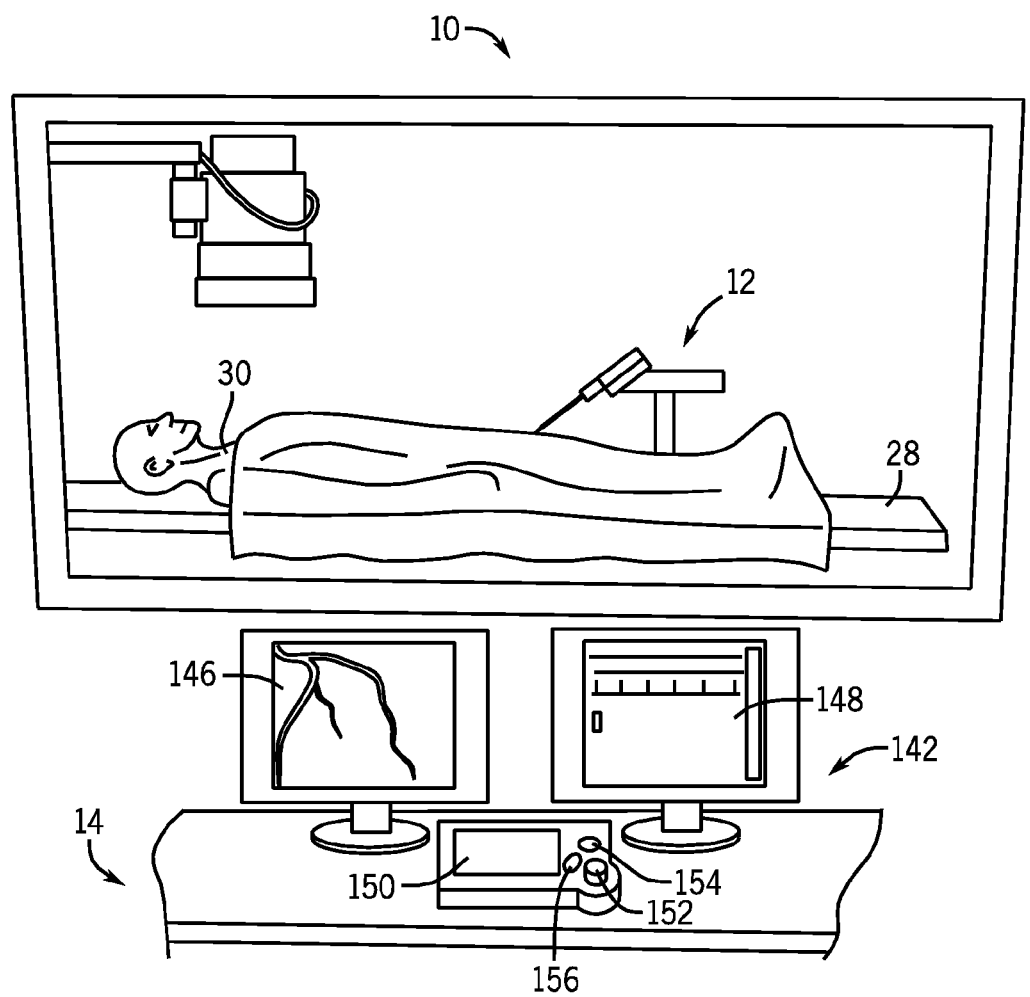
FIG. 1 is a perspective view of the robotic vascular catheter system.

Referring to FIG. 1, a robotic vascular catheter system 10 is used for performing interventional procedures, including performing a percutaneous coronary intervention ("PCI"). Discussion will proceed assuming a PCI is being performed. It should be noted, however, one skilled in the art would recognize that, although the system described is configured to perform a PCI, it is capable of performing a number of interventional procedures with minor adjustments. For more complex procedures, more than one robotic vascular catheter system 10 may be used.

Robotic vascular catheter system 10 comprises a bedside system 12 and workstation 14. The bedside system 12 comprises a motor controller, an articulating arm 18, an arm support 20, a motor drive base 22, a cassette 24, and a guide catheter support 26. Guide catheter support may be part of the cassette or alternatively may be a separate component that can be mounted to the cassette. Bedside system 12 is in communication with workstation 14, allowing signals generated by user inputs to workstation 14 to be transmitted to bedside system 12, controlling the various functions of beside system 12. Bedside system 12 also may provide feedback signals to workstation 14. Bedside system 12 may be connected to workstation 14 with a wireless connection means (not shown), with cable connectors (not shown), or with any other means capable of allowing signals generated by user inputs to workstation 14 to be transmitted to beside system 12.

Workstation 14 is capable of being remotely located, enabling robotic vascular catheter system 10 users to perform procedures outside the radiation zone, for instance, in either a procedure room or a separate control room. One benefit of remotely locating workstation 14 is that the need to wear heavy lead garments may be eliminated. This reduces orthopedic occupational hazards, including, but not limited to, spinal injuries and general strain on the body of the operator. A second benefit of remotely locating workstation 14 is that the dangers associated with radiation exposure are reduced. A third benefit of remotely locating workstation 14 is that it allows users to multitask outside the procedure room during downtime.

Bedside system 12 may be coupled to a standard table side bar (not shown) of a patient's bed 28 by locking bedside system 12 relative to a patient 30. The front of bedside system 12, and correspondingly cassette 24, is the end nearest the head of patient 30 when a procedure is being performed. The back of bedside system 12 is the end opposite the front. Coupling the bedside system to the bed or proximate the patient may be achieved using methods known in the art, including bolting bedside system 12 to the standard table side bar or using any other means sufficient to lock bedside system 12 relative to patient 30 and/or the bed. Ideally bedside system 12 is secured in a manner that is quick and easily to install. Bedside system 12 may be permanently coupled to the standard table side bar throughout numerous procedures, in one embodiment cassette 24 is replaced for different patients and/or different PCI procedures. However, bedside system 12 may be removably coupled to a bed for movement from one bed to another.

Cassette 24 is designed for a single use; it is disposable and should be replaced after each use. Cassette 24 may include a frangible component (not shown) that breaks off when cassette 24 is removed from motor drive base 22 to help ensure that cassette 24 is used for no more than a single use. Other mechanical means may be used to ensure a single use. For example, a portion of the cassette may be moved or manipulated in a way that does not permit the use of the cassette in another PCI procedure. Alternatively, cassette 24 may include an RFID (radio frequency identification) system (not shown) to identify when a cassette has been used. The cassette may include an RFID tag or other means of providing descriptive information identifying the type of cassette, particular features as well as a unique identifier for the particular cassette to distinguish it from any other cassette. Other components or systems capable of helping ensure that cassette 24 is used for no more than a single use may also be alternatively used. The fact that cassette 24 is designed for a single use has a number of benefits, including, but not limited to, helping maintain a sterility of robotic vascular catheter system 10 components and prevent patient-to-patient transmission of infections. The RFID system may permit the removal of the cassette for a short defined period of time, to enable resetting of the cassette, if it should fail to be securely attached in the first instance. The system could recognize the unique cassette by its unique identification from the RFID signal and allow the same cassette to be reintroduced only within a very short window of time that would suggest the cassette was being repositioned and not being used for another patient. It is also possible that the cassette may formed from materials that can be sterilized and reused, or certain components may be replaced that come into contact with bodily fluids.

FIG. 2 illustrates a preferred embodiment of robotic vascular catheter system 10. Articulating arm 18 is coupled to and protrudes outward from arm support 20. Motor drive base 22 is coupled to articulating arm 18. Cassette 24 is coupled to the top of motor drive base 22.

Articulating arm 18 is configured to be locked into infinite positions relative to patient 30. In a preferred embodiment, articulating arm 18 includes a first knuckle 32 and a second knuckle 34. First knuckle 32 enables articulating arm 18 to pivot about a vertical axis and or a horizontal axis. Second knuckle 34 enables articulating arm 18 to pivot up and down or about a horizontal axis. Articulating arm 18 may have multiple degrees of freedom to position cassette 24 in any orientation relative to the patient for proper positioning. Once the user has adjusted articulating arm 18, articulating arm 18 is locked into place by an articulating arm locking mechanism, preventing unwanted movement during the procedure. Articulating arm locking mechanism may be locked and unlocked mechanically, using a solenoid, or using any other mechanism capable of locking articulating arm 18, along with motor drive base 22 and cassette 24, relative to patient 30.

Referring to FIG. 3, bedside system 12 illustrated in FIG. 2 is shown before cassette 24 is attached to motor drive base 22. Motor drive base 22 includes a housing 38 and a plurality of capstans 40. Capstans 40 extend vertically to facilitate alignment with cassette 24 when coupling motor drive base 22 and cassette 24. Cassette 24 includes a housing 42, a cover 44 pivotally attached to housing 42, and a plurality of capstan sockets 46 corresponding to capstans 40 on motor drive base 22 to facilitate alignment with motor drive base 22 when coupling cassette 24 and motor drive base 22. In one embodiment capstans 40 extend generally upward and are matingly received in capstan sockets 46 that are located on the bottom surface of cassette 24. This permits cassette 24 to be placed onto motor drive base 22 in a generally downwardly direction. It is contemplated that motor drive base 22 and cassette 24 will be at an angle relative to a horizontal plane in an operative position to direct the guide catheter, guide wire and working catheter in a downwardly sloping direction toward the patient. Capstans 40 and capstan sockets 46 are one embodiment of a motor coupler, coupling the motors to axial and rotation drive mechanisms in the cassette. The capstans 40 and capstan sockets 46 may have gearing to allow a rotational force to be transmitted from motors located in the motor drive base 22 to the axial and rotational drive mechanisms within the cassette. While the capstans and capstan sockets allow the cassette to be placed downwardly onto the motor drive base, other motor couplers that can couple the motors to the drive mechanisms are also contemplated. In one embodiment the motors are located in the motor drive base 22. However, the motor drive base 22 may also be used to transmit force from motors located away from the motor drive base that are operatively coupled to the motor drive base with a mechanical linkage such as a cable or other mechanical coupler. It is also contemplated that the mechanical linkage could directly connect the motors to the capstan sockets so that the motor drive base 22 provides support for the cassette 24 and permits coupling of the cassette capstan sockets to the motors.

As illustrated in FIG. 2A, cover 44 may be opened to provide access to the mechanisms within cassette 24 to help facilitate loading and unloading of the guide wire and catheter instruments within the cassette 24. Cover 44 may include a wall member used to help positively locate the guide wire within the transmission mechanisms as described more fully below. Cover 44 may be secured by a hinge or other pivot enabling members. Alternatively, cover 44 may be secured in an up down arrangement. The movement of cover 44 from a closed to open position may cause the release of the guide wire or other catheter instruments from the transmission mechanisms.

Before coupling cassette 24 to motor drive base 22, a sterile, plastic cover (not shown) is draped over articulating arm 18 and motor drive base 22. The sterile, plastic cover includes pre-cut holes (not shown) that correspond to capstans 40 on motor drive base 22. The sterile, plastic cover shields the sterilized components of robotic vascular catheter system 10 from the unsterilized components, including motor drive base 22, articulating arm 18, and arm support 20. Cassette 24 is sterile before use. Once cassette 24 has been coupled to motor drive base 22 and used, it is disposed of and replaced with another sterile, single-use cassette.

Referring to FIGS. 6-9, cassette 24 further includes a first axial drive mechanism 48 for driving a guide wire 50 along its longitudinal axis, a second axial drive mechanism 52 for driving a working catheter 54 along its longitudinal axis, a first rotational drive mechanism 56 enabling guide wire 50 to rotate while still permitting guide wire 50 to be independently moved along its longitudinal axis. Working catheter 54 may be embodied as a balloon, stent on a delivery catheter, a stent with a balloon, or any other therapeutic or diagnostic catheter device; these embodiments are collectively referred to as working catheter 54. In one embodiment first axial drive mechanism 48 and first rotational drive mechanism 56 are positioned substantially in series along a longitudinal axis 60 of cassette 24. In one embodiment, second axial drive mechanism 52 is positioned at an angle to first axial drive mechanism 48.

After coupling cassette 24 to motor drive base 22 and before using robotic vascular catheter system 10 for a procedure, guide wire 50 and working catheter 54 must be loaded into the drive mechanisms in cassette 24. To load cassette 24, the user opens cover 44. Upon opening cover 44, an engagement-disengagement mechanism is activated, causing the drive mechanisms to automatically adjust for quick access. When cassette 24 is in open cover position, the drive mechanisms are in position for loading guide wire 50 and working catheter 54. Upon closing cover 44, the engagement-disengagement mechanism is activated, causing the drive mechanisms to automatically adjust, releasably engaging guide wire 50 and working catheter 54. Alternatively, it may be possible to engage and/or disengage guide wire 50 when cover 44 is in an open position. When cassette 24 is in closed cover position, the drive mechanisms apply sufficient pressure to guide wire 50 and working catheter 54 to be able to drive them. In a preferred embodiment, cover 44 is formed from a clear, translucent material to permit viewing of the drive mechanisms while cover 44 is closed, in closed cover position. Though, one of skill in the art would recognize that a variety of other materials are suitable. It may also be possible to disengage the drive mechanisms with a mechanical switch or electromechanical device with or without first opening the cover. Disengagement of the drive mechanisms will result in the surfaces of the pinch rollers of the axial drive mechanisms and the engagement surfaces of the rotational drive mechanism moving away from one another to allow easy removal and insertion of the guide wire and working catheter. At least one of the pinch rollers is supported by at least one disengagement mechanism that physically moves the pinch roller surfaces away from one another. Similarly, the engagement surfaces of the rotational drive mechanism are also operatively connected to a disengagement mechanism to physically move the engagement surfaces of the rotational drive mechanism away from one another. The pinch rollers are in a disengagement position when the pinch roller surfaces are positioned apart from one another.

Cassette 24 further includes a system to self-test the cassette upon loading (not shown). The system for self-testing cassette loading may be activated by an operator at workstation 14. Alternatively, the system may automatically initiate a self-test of the cassette upon closing of cover 44 to test each of the drive mechanisms. Feedback from the motors to workstation 14 could confirm proper seating of the cassette within the base. In addition to testing that each of the motors are properly secured to the cassette, each transmission mechanism may be activated to move the guide wire and/or working catheter a predetermined distance or rotation and then measure the distance actually moved or rotated by use of sensors. If the movement conforms to the predetermined parameters the system is shown to be working and operational. When the detected movement of the guide wire and/or working catheter does not conform to set parameters the system will show an error message.

Cassette 24 is designed with ergonomic considerations in mind, handle 64 enables easy manipulation and movement of the cassette and cassette base by an operator to position the system relative to the patient. Cover 44 may include a latch 210 located on the inside surface of the cover or in within the housing of the cassette to hold guide wire 50 during exchanges or when manipulating more than one wire. Catheter system 10 may include system for inflating working catheter 54, and a system for injecting a contrast media. Specifically, work station 14 may include a control mechanism for remotely controlling a pump for the injection of a contrast media.

Figure 9:
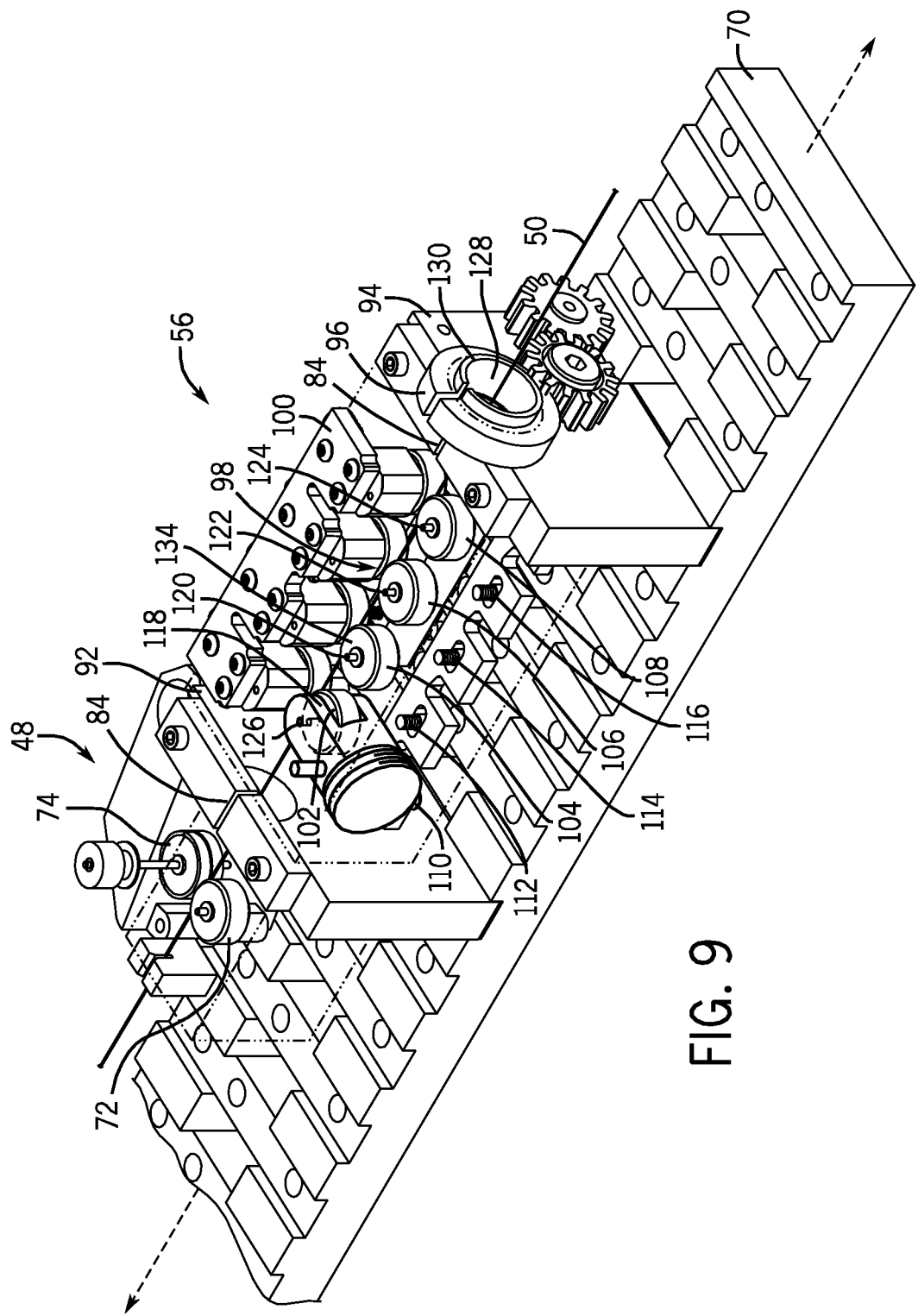
FIG. 9 is a perspective view of a portion of the cassette illustrating the rotational and axial drive systems.

Referring to FIG. 9 cassette 24 is shown without cover 44 and without housing 42. Cassette 24 includes a base plate 70 that supports first axial drive mechanism 48 and first rotational drive mechanism 56. Axial drive mechanism 48 and rotational drive mechanism 56 are positioned and secured consecutively/in series along a longitudinal axis of base plate 70. First axial drive mechanism 48 is shown positioned closer to the back end of cassette 24, behind first rotational drive mechanism 56. It should be noted, however, that first rotational drive mechanism 56 may be positioned behind first axial drive mechanism 48. It is believed that positioning rotational drive mechanism 56 closer to the patient provides for increased control of rotation of the guide wire, since any pressure and/or friction from the rollers in axial drive mechanism 48 is located distal the patient.

Figure 10:
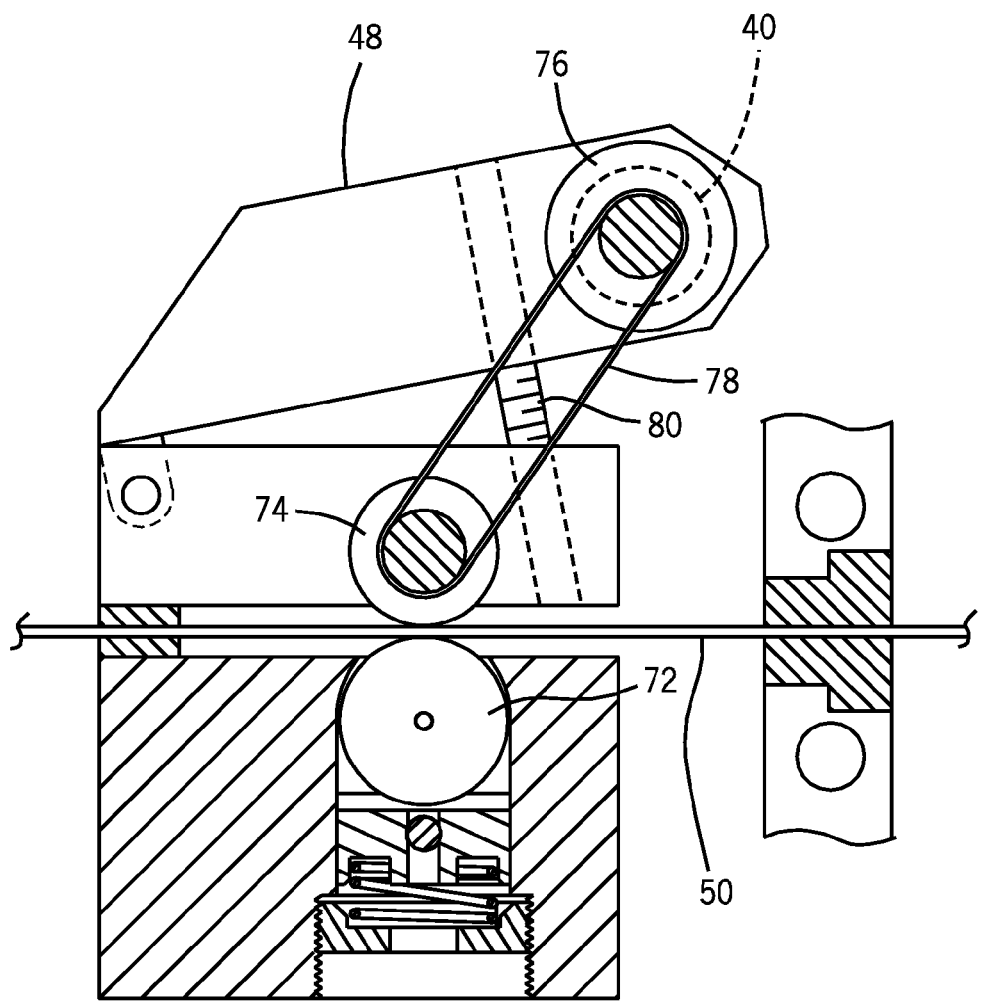
FIG. 10 is a cross sectional view of the axial drive system.

Referring to FIGS. 9 and 10, first axial drive mechanism 48 includes a first roller 72 and a second roller 74 working in cooperation to drive guide wire 50 in an axial direction. First roller 72 is spring biased toward second roller 74 with sufficient force to provide movement to guide wire 50 upon rotation of rollers 72, 74. It may be possible to adjust the spring force to ensure proper operation of the system. The spring force is set to allow rotation of guide wire 50 about its axis. In one embodiment first roller 72 has a first engagement surface and second roller 74 includes a second engagement surface. Guide wire 50 is removably placed between the first and second engagement surfaces of the first and second rollers 72 and 74 respectively. A solenoid may be used to move first roller and second roller closer toward and away from one another to capture and release guide wire between first and second rollers 72, 74. A solenoid may be used to move a holder supporting one of the rollers toward the other roller. A spring on the holder may be employed to bias one roller toward the other roller to provide a sufficient force on the guide wire 50 to effectively permit translation of the guide wire along its longitudinal axis upon rotation of at least one of the rollers.

Second roller 74 is driven by a drive gear or roller 76 via a belt 78. Sufficient tension is applied to belt 78 via a tension member 80. However, second roller 74 may be driven directly from one of the capstans 40 in motor drive base 22.

In alternative embodiments, pair of rollers 72, 74 may comprise a roller and an anvil or a roller and any grip surface wherein the pressure between that grip surface and a roller is sufficient to drive guide wire 50 along its longitudinal axis.

Figure 11:
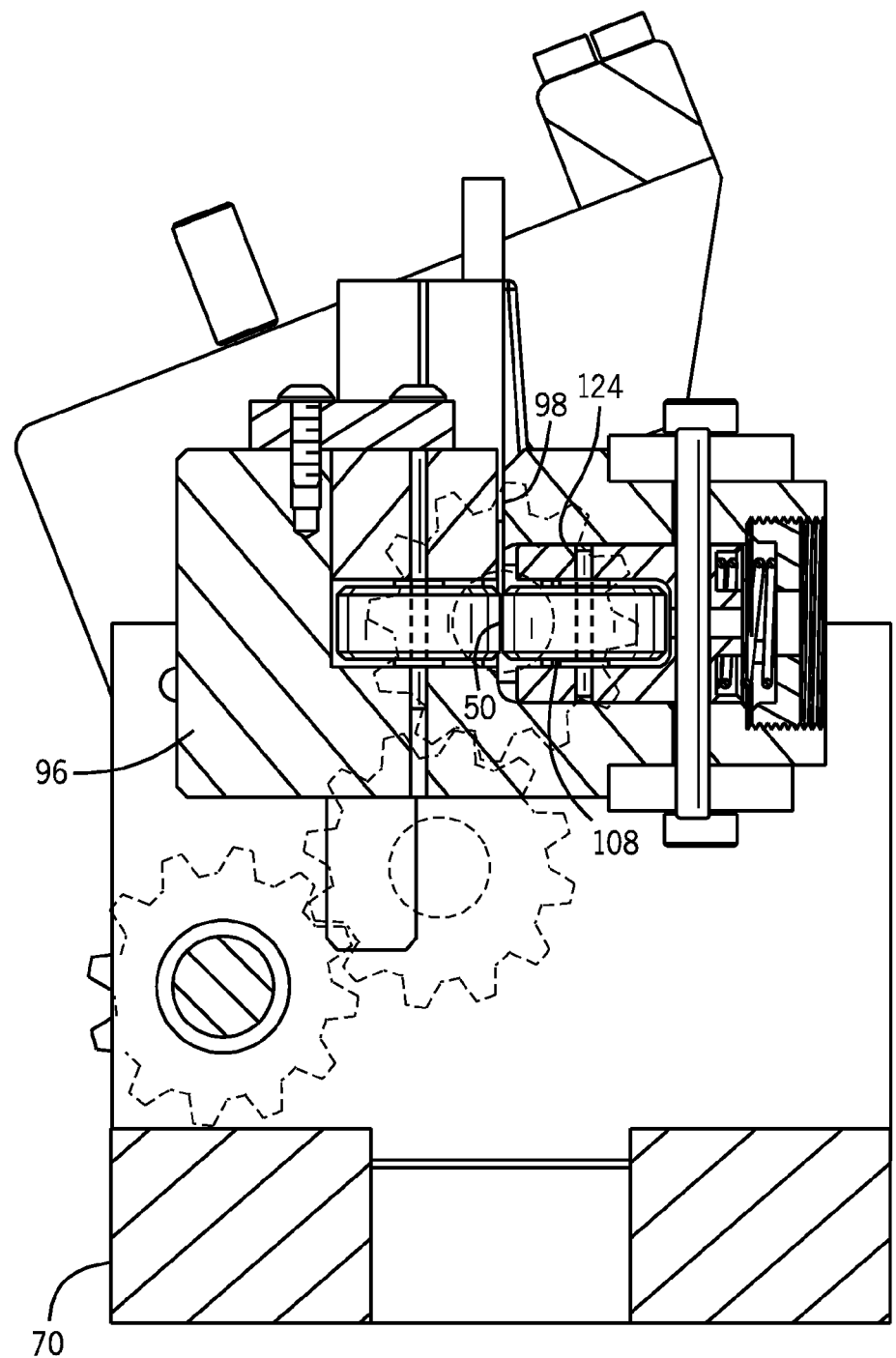
FIG. 11 is a cross sectional view of the rotational drive taken generally about line 11-11 of FIG. 6.
Figure 14:
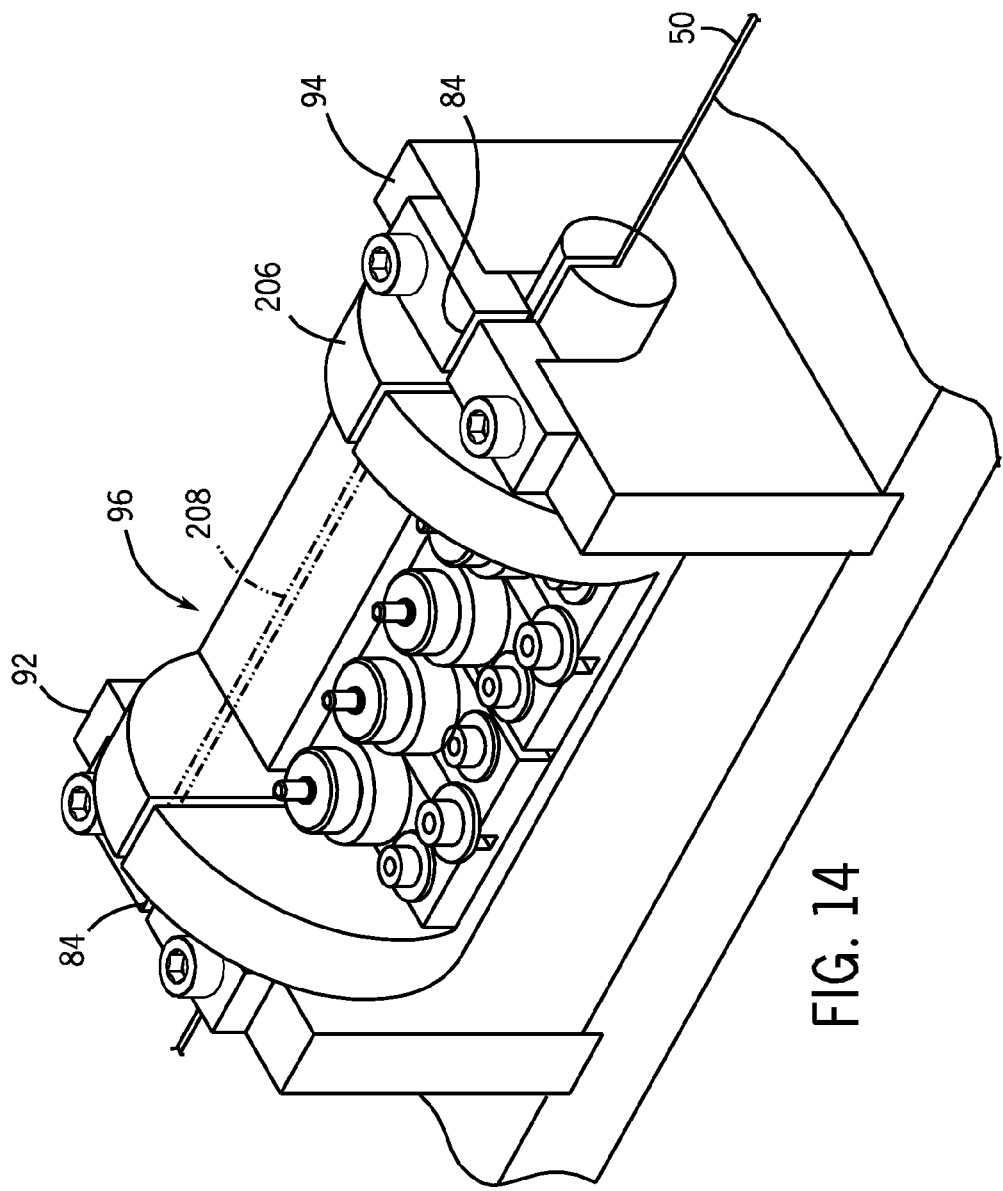
FIG. 14 is a perspective view of a portion of the cassette with one embodiment of a rotating assembly.

Further referring to FIGS. 6, 9 and 11, first rotational drive mechanism 56 includes a first rotational drive mechanism supporting block 92, a second rotational drive mechanism supporting block 94, and a rotational drive mechanism 96. Rotational drive mechanism 96 includes a plate 100, four pairs of rollers 102, 104, 106, 108, four pairs of roller fasteners 110, 112, 114, 116, supported on four pairs of roller axles 118, 120, 122, 124, a rotational drive mechanism comb, a longitudinal axis 128, and a pair of cylindrical protrusions 130 that extend through and are supported in a bore in each of supporting blocks 92 and 94. Pair of cylindrical protrusions 130, 132 are substantially concentric with rotational drive mechanism 96, extending outward from either end of rotational drive mechanism 96 along its longitudinal axis 128. First rotational drive mechanism supporting block 92 and second rotational drive mechanism supporting block 94 are transverse to longitudinal axis 128 of base plate 70 and are spaced out along the longitudinal axis of base plate 70 a distance sufficient to accommodate rotational drive mechanism 96 between them. Rotational drive mechanism 96 is suspended and secured between first rotational drive mechanism supporting block 92 and second rotational drive mechanism supporting block 94 over base plate 70 by pair of cylindrical protrusions 130, 132, which also serve as a path for guide wire 50 to extend. Referring to FIG. 14 the elements of rotational drive mechanism 96 may be supported on a rotating assembly 206 that rotates between supporting blocks 92 and 94.

Each supporting block 92, 94 includes a guide wire slit 84 extending substantially radially outward from the longitudinal axis 128 of rotational drive mechanism 96. Each of the four pairs of rollers 102, 104, 106, 108 meets along a longitudinal axis of rotational drive mechanism 96. Four pairs of rollers 102, 104, 106, 108 and four pairs of roller fasteners 110, 112, 114, 116 are positioned over four pairs of axles 118, 120, 122, 124 with four pairs of roller fasteners 110, 112, 114, 116 fixing four pairs of rollers 102, 104, 106, 108 along four pairs of axles 118, 120, 122, 124. While rotational drive mechanism is described with four pair of rollers, it may be possible to use a single pair of rollers, two or three pair of rollers or more than four pair of rollers. Referring to FIG. 14 an element 208 is illustrated that represents the path that guide wire 50 would extend through when the rotating assembly is in the load and unload position. When the rotating assembly is in the load and unload position the path represented by element 208 is in alignment with guide wire slits 84 in supporting blocks 92 and 94 that are illustrated in FIG. 9.

When cover 44 of cassette 24 is in the closed position, a rotational drive mechanism locator may be used to assist in the positioning of guide wire 50 downward toward the longitudinal axis of rotational drive mechanism 96 to help locate and maintain guide wire 50 between the four pairs of rollers 102, 104, 106, 108. Guide wire 50 is releasably engaged between four pairs of rollers 102, 104, 106, 108 in first rotational drive mechanism 56. When robotic vascular catheter system 10 is used during a procedure, the rollers within the engagement surfaces of the four pairs of rollers 102, 104, 106, 108 move toward one another to apply sufficient pressure to rotate guide wire 50 upon rotation of rotational drive mechanism 96 while still permitting guide wire 50 to be independently moved along its longitudinal axis by axial drive mechanism 48. The rotation of guide wire 50 results from the torque imparted on guide wire 50 because of the frictional forces between four pairs of rollers 102, 104, 106, and 108 during rotation of rotational drive mechanism 96. The rollers in the pairs of rollers 102-108 are free to rotate about their vertical axis allowing a guide wire 50 to move axially. The pressure between each pair of rollers is sufficient to impart a rotation to a guide wire 50 located therebetween when the entire rotational drive mechanism is rotated. The rollers may be moved away from one another to permit easy insertion and removal of guide wire 50 to load and unload the guide wire within the rotational drive mechanism. One set of the rollers may be moved away from the other set of rollers when cover 44 is in the open position and allowed to move back toward the other set of rollers when cover 44 is in a closed position. In order to easily remove or insert guide wire 50 into rotational drive mechanism 96 between the rollers a vertical path 98 must align with guide wire slit 84. When cover 44 is opened, the rotational drive mechanism rotates to a load/ unload position in which vertical path 98 is aligned with guide wire slit 84 thereby allowing easy insertion and/or removal of guide wire 50 from the rotational drive mechanism. In an alternative embodiment, the rollers do not move away from one another but allow for manual insertion and removal of guide wire 50 between the rollers. The manual insertion may be permitted by the flexibility of the rollers themselves or by permitting one of the spring biased rollers to move away from the second in the pair of rollers to allow insertion of guide wire 50.

Alternative embodiments of four pairs of rollers 102, 104, 106, 108 include, but are not limited to, more or less than four pairs of rollers. Also, four pairs of rollers 102, 104, 106, 108 comprise pairs of rollers and anvils, each roller paired up with an anvil and creating sufficient pressure to rotate guide wire 50 upon rotation of rotational drive mechanism 96 while still permitting guide wire 50 to be independently moved along its longitudinal axis. Similarly, four pairs of rollers 102, 104, 106, 108 may alternatively comprise a plurality of rollers and any grip surface where the pressure between each roller and that grip surface is sufficient to rotate guide wire 50 upon rotation of rotational drive mechanism 96 while still permitting guide wire 50 to be independently moved along its longitudinal axis. In another embodiment rotational drive mechanism may include two engagement surfaces that may or may not rotate in the axial direction of the longitudinal axis of the guide wire.

When cover 44 of cassette 24 is in open cover position, first axial drive mechanism 48 and first rotational drive mechanism 56 are positioned such to facilitate loading guide wire 50 and working catheter 54. In the insertion and removal position, guide wire slits 84 in supporting blocks 92, 94 and guide wire path 98 of rotational drive mechanism 96 are substantially aligned. Similarly, pair of rollers 72, 74 of first axial drive mechanism 48 and four pairs of rollers 102, 104, 106, 108 of first rotational drive mechanism 56 are substantially aligned. This enables guide wire 50 to extend through both first axial drive mechanism 48 and first rotational drive mechanism 56. As discussed above, each of the pair of rollers in the axial drive mechanism and rotational drive mechanism may move apart to facilitate easy insertion and removal of guide wire 50 when cover 44 is in the open position.

Further referring to FIG. 6 second axial drive mechanism 52 comprises a pair of rollers 136, and a working catheter channel 138. Pair of rollers 136 releasably engage working catheter 54 in working catheter channel 138. When cassette 24 is in open cover position, second axial drive mechanism 52 is positioned such to facilitate loading working catheter 54 between pair of rollers 136. When cover 44 of cassette 24 is closed, working catheter 54 is loaded and releasably engaged between pair of rollers 136. Alternate embodiments of second axial drive mechanism 52 include, but are not limited to, an embodiment wherein pair of rollers 136 comprises a roller and an anvil or a roller and any grip surface wherein the pressure between that grip surface and a roller is sufficient to drive working catheter 54 along its longitudinal axis. Other axial drive mechanisms are also contemplated and may be used.

Referring to FIG. 1 workstation 14 comprises a user interface 142. User interface 142 enables a user to enter commands controlling the axial motion of guide wire 50 via first axial drive mechanism 48, the axial motion of working catheter 54 via second axial drive mechanism 52, and the rotational motion of guide wire 50 via first rotational drive mechanism 56. In an alternative embodiment of robotic vascular catheter system 10, the user would additionally be capable of controlling a guide catheter 144 from workstation 14, in an axial and/or rotational manner.

In a preferred embodiment, user interface 142 includes a first screen 146 and a second screen 148. First screen 146 and second screen 148 are configured to present information and images potentially useful to a user of robotic vascular catheter system 10. User interface 142 further includes a touch screen 150, having a pair of joysticks 152 having variable speed control, a first jog button 154 for 1 mm jogs, and a second jog button 156 for 5 mm jogs. First jog button 154 and second jog button 156 have continuous jog capability. Depression of the jog buttons will move the guide wire 50 a set distance forward. Jog buttons may be used for movement of guide wire 50 and/or working catheter 54. Rotational Jog button may be set to rotate a pre-set degree or it may be set to rotate a selected degree. Another button may be used to accelerate the speed of the guide wire 50 or provide a multiplier so that the variable speed control reacts in a heightened manner. For example if movement of a joystick a set distance results in the movement of the guide wire at a set speed in normal operation, the guide wire would move at a multiple of the set speed by depressing the button to accelerate the speed.

In alternative embodiments, user interface 142 may have various configurations. For instance, touch screen 150 may be integrated with x-ray or other imaging data. In fact, a variety of data and controls may be integrated on a single screen, including, but not limited to, contrast media insertion control, balloon inflation control, image processing control(s), hemodynamic data, etc. Alternative joystick configurations include, but are not limited to separate joysticks may be provided for each drive mechanism, rather than two joysticks for controlling all drive mechanisms.

Robotic vascular catheter system 10 may further incorporate a number of safety features and conveniences (not shown). For instance, robotic vascular catheter system 10 may be capable of providing a mechanism for a user to manually override it during a procedure. In the event, that the operator must manually align the rotational drive mechanism to remove the guide wire 50, it is contemplated that the rotational drive mechanism can be moved to a load unload position so that the engagement surfaces in the rotational drive mechanism are separated and in line with the slits in rotational drive mechanism supports. Additionally, workstation 14 may incorporate a system allowing a user to voice-activate controls, a feature which could be overridden by an emergency stop. There may also be a force limitation mechanism. Robotic vascular catheter system 10 could have a pre-determined limit to the amount of force that could be placed on guide wire 50. If the motors were to apply a force greater than the pre-determined amount, a clutch act to disengage the wheels from the motors. For example if any of the drive mechanisms were to become stuck and unable to rotate a clutch mechanism would act to allow the motors to rotate without causing damage to the stuck drive mechanism or the motor itself.

Another possible feature is a slippage-detecting mechanism. Such a mechanism would provide a continuous check between the desired and actual movements of guide wire 50 or working catheter 54 and rollers, pair of rollers 72, 74 of first axial drive mechanism 48 and four pairs of rollers 102, 104, 106, 108 of first rotational drive mechanism 56. This mechanism could provide warnings when a given threshold has been crossed. This threshold may remain constant throughout a procedure or may vary depending on the location of system components in the heart. In one embodiment, an ancillary encoder (not shown) may be used to give the exact location of guide wire 50, in terms of both axial and rotational movement, and working catheter 54, in terms of axial movement, during a procedure. Pair of rollers 72, 74 and four pairs of rollers 102, 104, 106, 108 would be positioned near a plurality of idler rollers 158 that check the movement of the robotic vascular catheter system 10, comparing the movement of the rollers to motor movement. Note that these features and conveniences are exemplary and should not be read to be exhaustive.

Referring to FIGS. 3, 7, 8 and 13 in a preferred embodiment cassette 24 further includes a coupling mechanism 162 for securing a y-connector 160 attached to a guide catheter 144 and a guide catheter support arm, shown as a rod 164. Coupling mechanism 162 releasably secures y-connector 160. Y-connector 160 connects to guide catheter 144. Y-connector 160 further provides a means for administering drugs to a patient during the PCI procedure. In one embodiment, robotic vascular catheter system 10 provides a user the ability to remotely control drug administration through y-connector 160. Guide catheter 144 may be able to pivot about its longitudinal axis independent of y-connector 160. The y-connector includes three legs. A first leg is attached to the guide catheter 144. A second leg is angled away from the longitudinal axis of the guide catheter to permit introduction of a contrast agent or medicine. A one way valve prohibits bodily fluid from exiting the second leg. A third leg extends away from the guide catheter and allows insertion of a working catheter and guide wire through the y-connector. The third leg also includes a one way valve that permits insertion and removal of the working catheter and guide wire but prohibits bodily fluids from exiting the third leg.

A rod 164 is coupled to cassette 24 at a point along the front end of cassette 24 and supports guide catheter support 26 at its other end. Rod 164 is adjustable, and capable of translating away from cassette 24 and back towards cassette 24 and moving independently of cassette 24, to help position guide catheter 24 using methods known in the art. In alternative embodiments, rod 164 may take on any number of configurations capable of supporting guide catheter support 26 and guide catheter 144. For example, guide rod 164 may include telescoping segments.

Guide catheter support 26, shown as a spring-loaded clamp, provides support for guide catheter 144. Guide catheter support 26 is at a point between the front end of cassette 24 and patient 30 during a procedure. In this position, guide catheter support 26 helps prevent unwanted movement of the guide catheter 144 and its contents, affording greater accuracy when performing a procedure.

Referring to FIG. 6, when guide wire 50 and working catheter 54 have been loaded in robotic vascular catheter system 10, cover 44 of cassette 24 is closed guide wire 50 extends out of the back end of cassette 24 through an opening in housing 42. Moving toward the front end of cassette 24, guide wire 50 passes through first axial drive mechanism 48, through first rotational drive mechanism 56, and then converges with working catheter 54 at a convergence zone 166. Working catheter 54 enters cassette 24 through a slot 168 in the side of housing 42. Before converging with guide wire 50 at convergence zone 166, working catheter 54 first passes through second axial drive mechanism 52. Working catheter 54 includes a hollow over the wire portion, which guide wire 50 passes into at convergence zone 166. Working catheter 54 with guide wire 50 in its over the wire portion exits the front end of cassette 24 through an opening 172. Cassette 24 may include a channel configured to constrain the working catheter along a predefined path from a first point where the longitudinal axis of the working catheter and the longitudinal axis of the guide wire are not coaxial to a point where the longitudinal axis of the working catheter and the longitudinal axis of the guiding catheter are co-axial. The path is located within the housing and may include a groove or other physical means to form at least a portion of the path.

Further referring to FIG. 6, y-connector 160 is connected to a proximal end of guide catheter 144. Guide catheter 144 has a central bore. Guide wire 50 and working catheter 54 pass through y-connector 160 into central bore 174 of guide catheter 144 upon exiting cassette 24 through opening 172. In a preferred embodiment, guide catheter 144 runs substantially parallel to rod 164 from y-connector 160 to guide catheter support 26, where it is releasably secured. Guide catheter support 26 facilitates movement of guide wire 50 and working catheter 54 within central bore 174 of guide catheter 144, by helping to keep guide catheter 144 straight.

Y-connector 160 is releasably secured to cassette 24 by coupling mechanism 162, shown in a preferred embodiment as a spring-biased clamp in FIGS. 7 and 8. Coupling mechanism 162 includes a frame 176, a handle 178, and at least one spring 180. Frame 176 includes a receiving portion 182 against which y-connector 160 is secured. Handle 178 includes a lever arm 184 and a capture portion 186. Capture portion 186 applies sufficient pressure to secure y-connector 160 against receiving portion 182 of frame 176 when lever arm 184 is not depressed. Handle 178 pivots about a pivot point 188. Springs 180 exert an upward force on lever arm 184 at a distance from pivot point 188, biasing capture portion 186 of handle 178 toward receiving portion 182 of frame 176. Referring to FIG. 8, when lever arm 184 is depressed, springs 180 are also compressed. Capture portion 186 of handle 178 pivots about pivot point 188, moving away from y-connector 160 and receiving portion 182 and releasing y-connector 160. Referring back to FIG. 7, when handle 178 is released lever arm 184 is again forced upward, pivoting about pivot point 188. Capture portion 186 moves in toward receiving portion 182 and y-connector 160, releasably securing y-connector 160.

Figure 4:
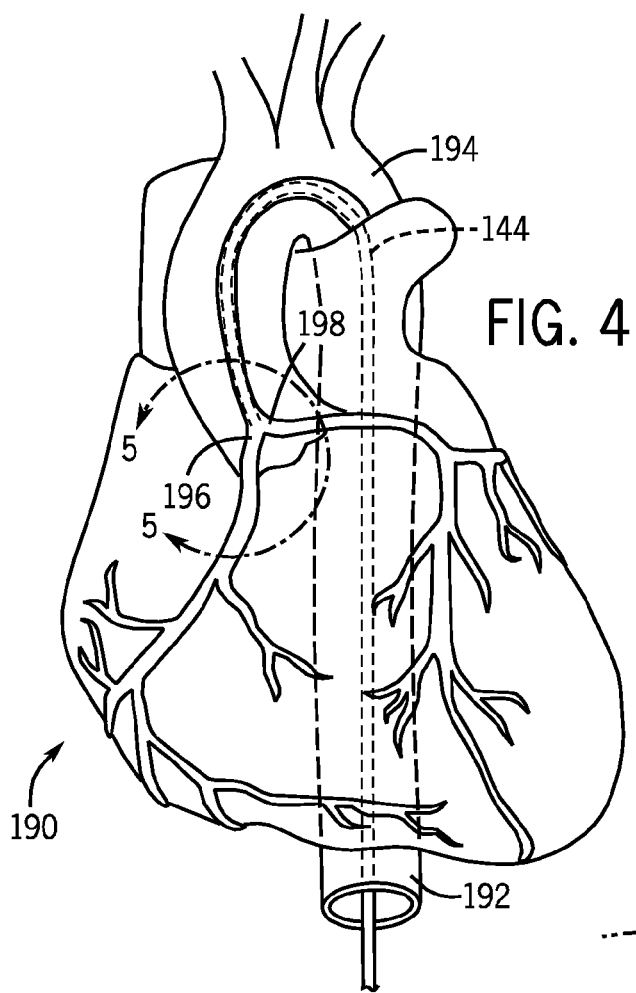
FIG. 4 is a view of a heart.

The exemplary procedure begins after a diagnostic procedure has been completed, leaving a diagnostic guide wire (not shown) in a heart 190 (shown in FIG. 4), heart 190 including an aorta 192 and an aortic arch 194. Before using robotic vascular catheter system 10, guide catheter 144 is run up into aorta 192 over the diagnostic guide wire, the diagnostic guide wire is removed, and guide catheter 144 is positioned into either a right ostium 196 opening to the right coronary artery or a left ostium 198 opening to the circumflex or left anterior descending arteries, depending where a lesion 200 is located. The shape of guide catheter 144 varies based on which ostium it is to enter. As discussed above, bedside system 12 is likely already fixed to patient's bed 28.

For the purposes of clarity, steps for advancing guide catheter 50 and working catheter 54 and loading bedside system 12 will be discussed separately and in turn. One of skill in the art would recognize that a number of the steps in the discussion are interchangeable without deviating significantly from the method.

Guide catheter 144 is attached to y-connector 160. A y-connector introducer (not shown) is placed into y-connector 160. Guide wire 50 is advanced through the y-connector introducer into guide catheter 144 and then removed. Working catheter 54 is loaded onto guide wire 50. Working catheter 54 is then manually advanced up into guide catheter 144 over guide wire 50 until it is near the free end of guide wire 50.

Cassette 24 is coupled to motor drive base 22 over the sterile, plastic cover. Articulating arm 18 is locked relative to patient 30 and cover 44 of cassette 24 is opened, activating engagement-disengagement mechanism, which causes the drive mechanisms to position for loading guide wire 50 and working catheter 54. Guide wire 50 is positioned into guide wire path 98 between four pairs of rollers 102, 104, 106, 108 of first rotational drive mechanism 56, and into guide wire slit 84 and pair of rollers 72, 74 of first axial drive mechanism 48. The back end of guide wire 50 extends outwardly through the back of housing 42 and may contain a guide wire holder or support to contain the length of guide wire not being used within the patient. Working catheter 54 is placed in working catheter channel 138 between pair of rollers 136 of second axial drive mechanism 52. After positioning guide wire 50 and working catheter 54, cover 44 of cassette 24 is closed, again activating the engagement-disengagement mechanism. Robotic vascular catheter system 10 is loaded, drive mechanisms having releasably engaged guide wire 50 and working catheter 54.

Y-connector 160 is releasably secured to cassette 24 by depressing handle 178, placing y-connector 160 between frame 176 and handle 178. In this manner guide catheter 144 is releasably secured to the cassette 24.

Figure 5:
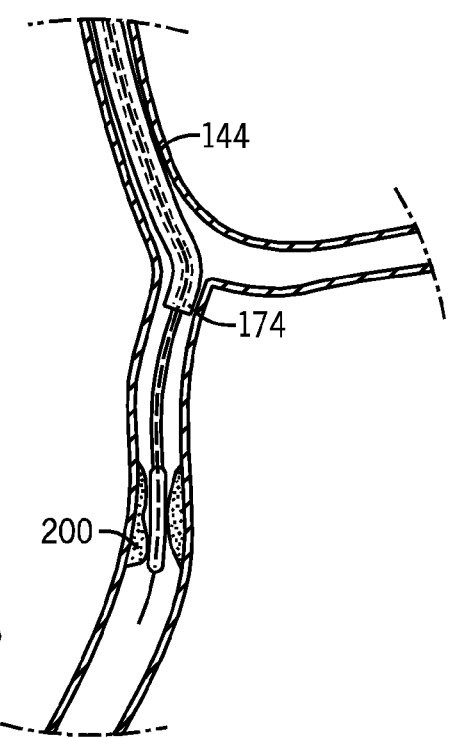
FIG. 5 is a view illustrating the guide catheter, the guide wire, and the balloon catheter within the heart.

The user operates the controls at workstation 14. In the above-discussed preferred embodiment of workstation 14, touch screen 150, a pair of joysticks 152, a first jog button 154, and a second jog button 156 are operated to direct the motion of guide wire 50 and working catheter 54. As shown in FIG. 5, guide wire 50 is typically moved and then followed by working catheter 54 until guide wire 50 is moved across lesion 200. Once guide wire 50 has crossed lesion 200, working catheter 54 is driven across, often fine tuning the position using first jog button 154, second jog button 156, or a combination of both.

Figure 12:
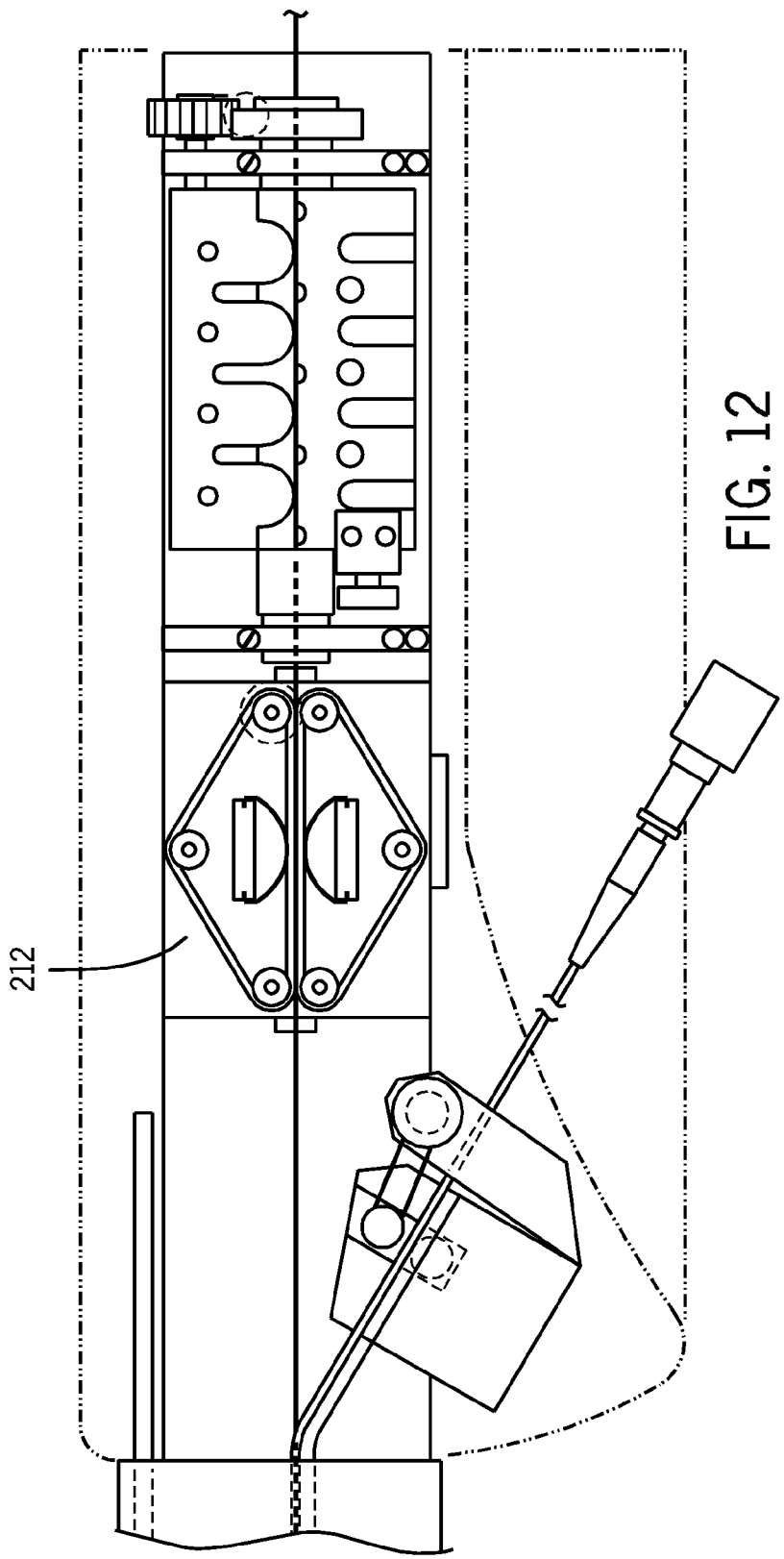
FIG. 12 is an alternative embodiment of a cassette system.

Referring to FIG. 12, an alternative axial drive 212 member may be used. For example pinch rollers may be replaced with a two belt mechanism.

Figure 13:
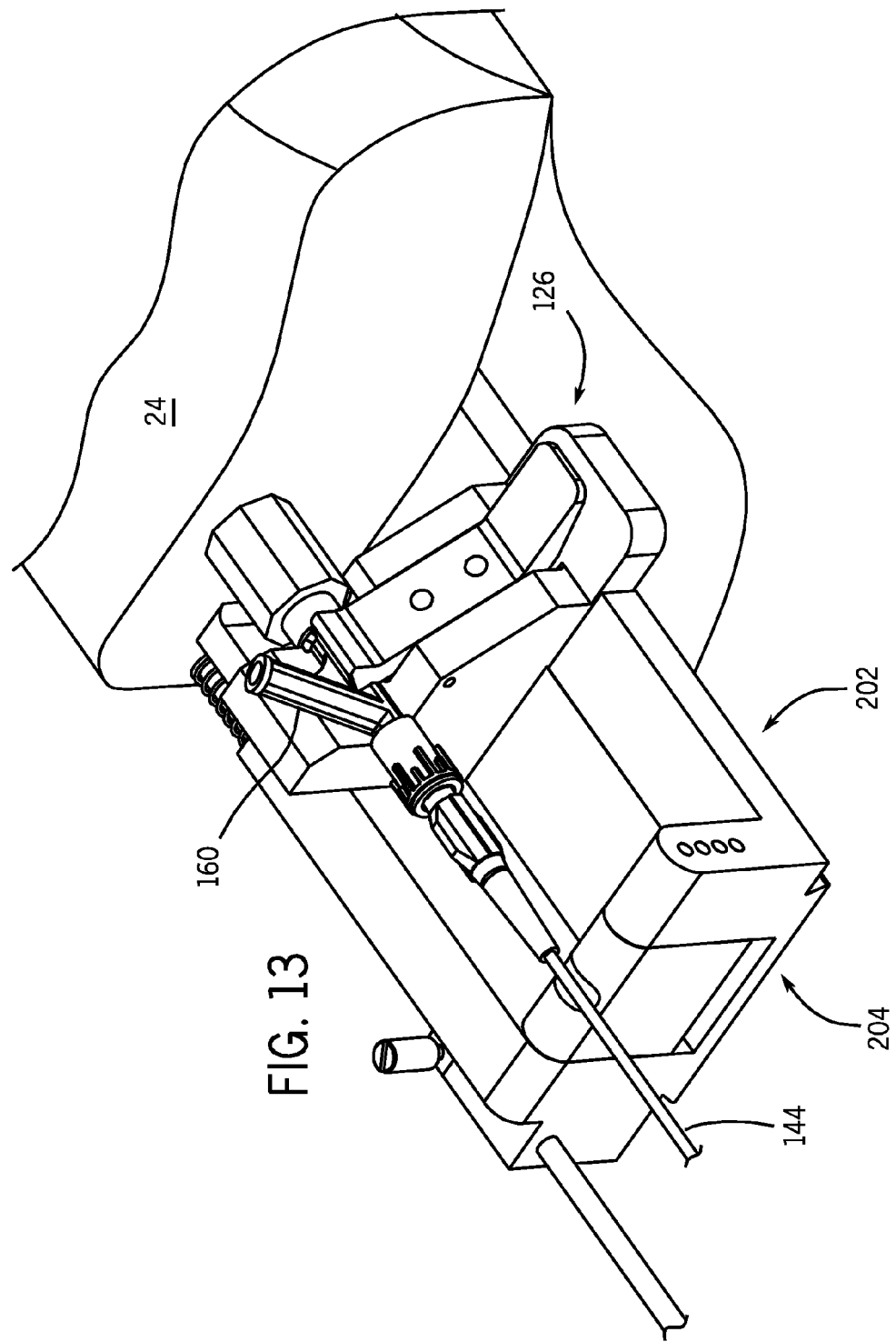
FIG. 13 is a perspective view of a portion of the cassette with a guiding catheter support shown in FIG. 3.

Referring to FIG. 13, cassette 24 includes a guide catheter support 202. Y-connector coupling mechanism is supported by guide catheter support 202. In an alternative embodiment, guide catheter support 202 may include a sled 204 that can be moved in a fore aft direction so that the guide catheter may be moved in a direction along its longitudinal axis. Cassette 24 may also include a drive mechanism to rotate sled 204 such that the guide catheter is rotated about its longitudinal axis, and a drive mechanism to move sled 204 in the fore aft direction such that the guide catheter may be moved along the longitudinal axis of the guide wire. The drive mechanisms used to move sled 204 may be located in the motor drive base 22 and move the sled 204 relative to cassette 24, so that sled 204 may be moved independently of the guide wire and/or working catheter.

Referring now to FIGS. 15 through 28C, another exemplary embodiment of a cassette for use with a robotic catheter system is shown. Similar to the embodiment discussed above, cassette 300 may be equipped with a guide wire 301 and a working catheter 303 to allow a user to perform a catheterization procedure utilizing cassette 300. In this embodiment, bedside system 12 includes a cassette 300 configured to be mounted to a motor drive base 302. FIG. 15 shows a bottom perspective view of cassette 300 prior to mounting to motor drive base 302. Motor drive base 302 includes a first capstan 304, a second capstan 306, and a third capstan 308, and cassette 300 includes a first capstan socket 310, a second capstan socket 312, and a third capstan socket 314. Cassette 300 includes a housing 316, and housing 316 includes a base plate 318.

Each of the capstan sockets is configured to receive one of the capstans of motor drive base 302. In the embodiment shown, base plate 318 includes a hole or aperture aligned with each of the capstan sockets 310, 312, and 314 to allow each capstan to engage with the appropriate capstan socket. The engagement between the capstans and capstan sockets allows the transfer of energy (e.g., rotational movement) generated by one or more actuators (e.g., motors) located within motor drive base 302 to each of the drive mechanisms (discussed below) within cassette 300. In one embodiment, a single actuator provides energy to each of the drive mechanisms. In another embodiment, there is an actuator that drives capstan 304, an actuator that drives capstan 306, and an actuator that drives capstan 308. Further, the positioning of the capstans and capstan sockets helps the user to align cassette 300 relative to motor drive base 302 by allowing cassette 300 to be mounted to motor drive base 302 only when all three capstan sockets are aligned with the proper capstan.

In one embodiment, the motors that drive capstans 304, 306, and 308 are located within motor drive base 302. In another embodiment, the motors that drive capstans 304, 306, and 308 may be located outside of base 302 connected to cassette 300 via an appropriate transmission device (e.g., shaft, cable, etc.). In yet another embodiment, cassette 300 includes motors located within the housing of cassette 300. In another embodiment, cassette 300 does not include capstan sockets 310, 312, and 314, but includes an alternative mechanism for transferring energy (e.g., rotational motion) from an actuator external to the cassette to each of the cassette drive mechanisms. For example, rotational movement may be transferred to the drive mechanisms of cassette 300 via alternating or rotating magnets or magnetic fields located within motor drive base 302.

In the embodiment shown, cassette 300 also includes a guide catheter support 311 that supports guide catheter 317 at a position spaced from cassette 300. As shown, guide catheter support 311 is attached to cassette 300 by a rod 313. Rod 313 and guide catheter support 311 are strong enough to support guide catheter 317 without buckling. Guide catheter support 311 supports guide catheter 317 at a position spaced from the cassette, between the patient and the cassette to prevent buckling, bending, etc. of the portion of guide catheter 317 between the cassette and the patient.

Referring to FIG. 16, cassette 300 is shown mounted to motor drive base 302. As shown in FIG. 16, cassette 300 includes an outer cassette cover 320 that may be attached to housing 316. When attached to housing 316, outer cassette cover 320 is positioned over and covers each of the drive mechanisms of cassette 300. By covering the drive assemblies of cassette 300, outer cassette cover 320 acts to prevent accidental contact with the drive mechanisms of cassette 300 while in use.

Figure 17:
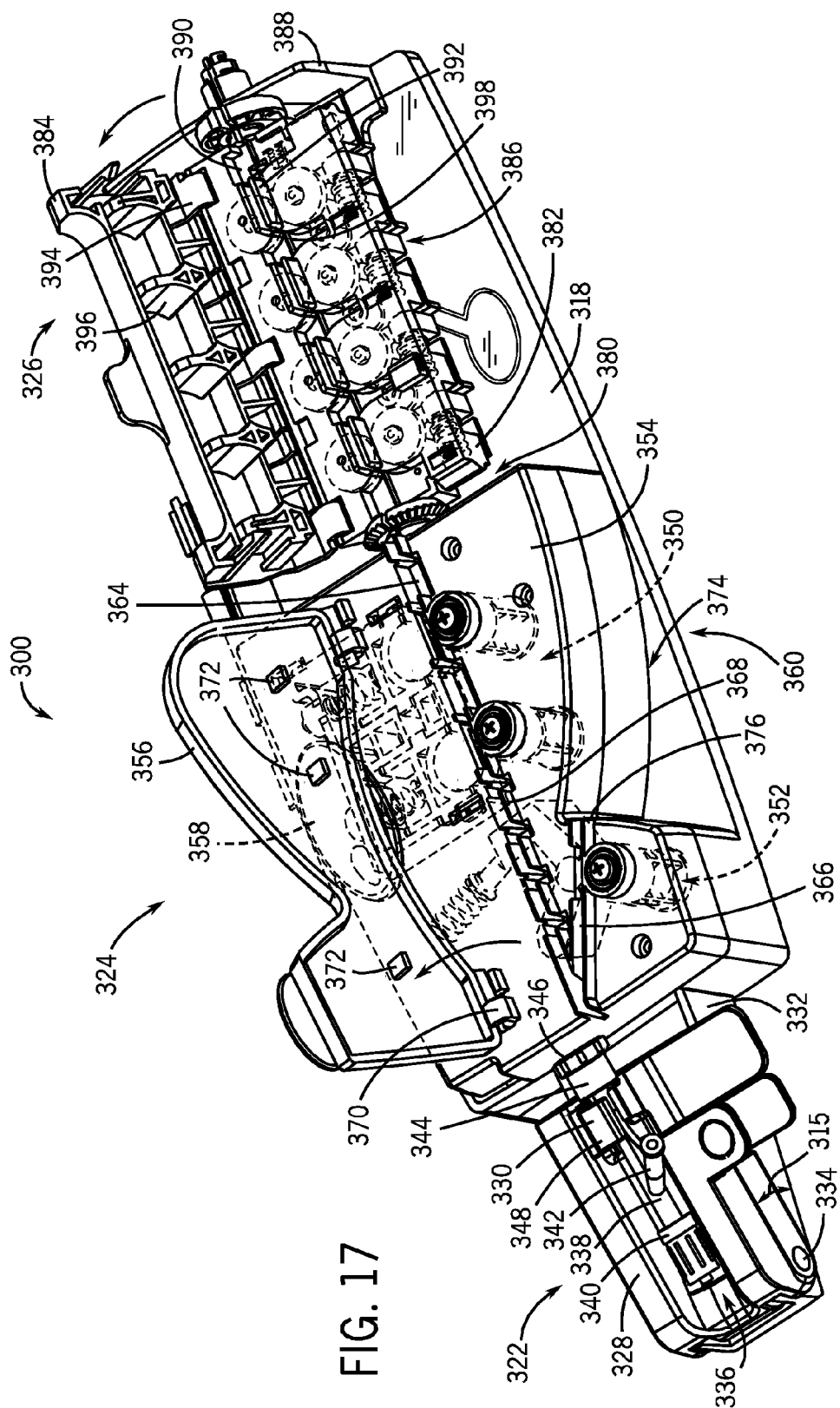
FIG. 17 is a perspective view of a cassette in the "loading" configuration.

Referring to FIG. 17, cassette 300 is shown in the "loading" configuration with outer cassette cover 320 removed. Cassette 300 includes a y-connector support assembly 322, an axial drive assembly 324, and a rotational drive assembly 326. Generally, the various portions of cassette 300 are placed in the loading configuration to allow the user to load or install a guide wire and/or working catheter into cassette 300. Further, in the exemplary embodiment shown, y-connector support assembly 322 is located in front of axial drive assembly 324, and axial drive assembly 324 is located in front of rotational drive assembly 326 within cassette 300.

Y-connector support assembly 322 includes a chassis 328 and a y-connector restraint 330. Base plate 318 includes a support arm 332 that supports y-connector support assembly 322. Chassis 328 is coupled to the front of support arm 332 via pin connection 334.

A central groove or depression 336 extends the length of chassis 328. Y-connector 338 rests within central groove 336 of chassis 328. Y-connector 338 includes a first leg 340, a second leg 342, and a third leg 344. First leg 340 is configured to attach to a guide catheter such that the central lumen of the y-connector is in fluid communication with the central lumen of the guide catheter. Second leg 342 is angled away from the longitudinal axis of y-connector 338. Second leg 342 of y-connector 338 allows introduction of a contrast agent or medicine into the lumen of the guide catheter. A one way valve prohibits bodily fluid from exiting second leg 342. Third leg 344 extends away from the guide catheter toward axial drive assembly 324. In use, guide wire 301 and working catheter 303 are inserted into third leg 344 of y-connector 338 via opening 346 and may be advanced through y-connector 338 into the lumen of the guide catheter. The third leg also includes a one way valve that permits insertion and removal of the working catheter and guide wire but prohibits bodily fluids from exiting third leg 344.

Chassis 328 is rotatable about an axis defined by pin connection 334 to allow chassis 328 to be placed in the "loading position" shown in FIG. 17. In the loading position, chassis 328 is positioned at about a 45 degree angle, shown by angle line 315, relative to support arm 332. Chassis 328 is moved to the "loading position" to provide easier access to opening 346 of the third leg 344 allowing the user to feed guide wire 301 and working catheter 303 into y-connector 338.

Y-connector support assembly 322 includes y-connector restraint 330. Y-connector restraint 330 is configured to releasably engage y-connector 338. In the engaged position shown in FIG. 17, engagement arm 348 of y-connector restraint 330 engages or presses y-connector 338 into central groove 336 to securely hold y-connector 338. Y-connector restraint 330 may be moved to a disengaged position to release y-connector 338 from chassis 328.

Cassette 300 also includes an axial drive assembly 324. Axial drive assembly 324 includes a first axial drive mechanism, shown as guide wire axial drive mechanism 350, and a second axial drive mechanism, shown as working catheter axial drive mechanism 352. Axial drive assembly 324 also includes a top deck 354, a cover 356, and a latch or handle 358.

Generally, guide wire axial drive mechanism 350 is configured to releasably engage and drive (e.g., to impart motion to) guide wire 301 along its longitudinal axis. In this manner, guide wire axial drive mechanism 350 provides for advancement and/or retraction of guide wire 301. Working catheter axial drive mechanism 352 is configured to releasably engage and drive (e.g., to impart motion to) working catheter 303 along its longitudinal axis. In this manner, working catheter axial drive mechanism 352 provides for advancement and/or retraction of working catheter 303.

Top deck 354 is mounted to a central portion 360 of base plate 318. Top deck 354 includes a guide wire channel 364 and a working catheter channel 366. Guide wire channel 364 is positioned generally perpendicular to the top surface of top deck 354 and runs the length of top deck 354 in the longitudinal direction. Working catheter channel 366 is positioned generally perpendicular to the top surface of top deck 354 and is located at an angle relative to guide wire channel 364. A plurality of tabs 368 extend vertically from the top surface of top deck 354 along guide wire channel 364.

In FIG. 17, cover 356 is shown in the open position. Handle 358 is moved to a position generally parallel to the longitudinal axis of cassette 300 to allow cover 356 to move to the open position. Cover 356 is mounted to top deck 354 via hinges 370. Cassette 300 includes a restraint structure that acts to restrain movement of the guide wire when cover 356 is in the closed position. As shown, the restraint structure includes a plurality of tabs 372 extending from the lower surface of cover 356. Tabs 372 are positioned such that when cover 356 is closed, tabs 372 are positioned within a portion of guide wire channel 364 between tabs 368 such that tabs 372 restrain movement of guide wire 301 in a vertical direction (i.e., restrains movement of the guide wire in a direction perpendicular to the top surface of top deck 354).

When cover 356 is in the open position, both guide wire axial drive mechanism 350 and working catheter axial drive mechanism 352 are exposed allowing the user to load cassette 300 with a guide wire and working catheter. With cover 356 open, guide wire 301 is loaded into axial drive assembly 324 by placing the guide wire into guide wire channel 364. Tabs 368 facilitate the placement of guide wire 301 by aiding the user in aligning the guide wire with guide wire channel 364. In addition, working catheter 303 is loaded into axial drive assembly 324 by placing the working catheter into working catheter channel 366. As will be described in more detail below, once the guide wire and working catheter are positioned within guide wire channel 364 and working catheter channel 366, respectively, engagement surfaces of guide wire axial drive mechanism 350 and working catheter axial drive mechanism 352 are brought into engagement with the guide wire and working catheter respectively.

Both top deck 354 and central portion 360 of base plate 318 are shaped to define a recess 374. Working catheter channel 366 includes an opening 376 located within recess 374. Recess 374 allows opening 376 to be closer to y-connector 338 and also closer to the entry incision allowing working catheter 303 to be advanced farther into the patient's vascular system than if opening 376 were located further away from y-connector 338 or the entry incision. As can be seen in FIG. 16, working catheter 303 includes a hub 305 at its proximal end that is too large to fit through opening 376. Thus, the closer that opening 376 is to y-connector 338 and to the entry incision the further working catheter 303 can be advanced into the patient's vascular system.

Cassette 300 also includes a rotational drive assembly 326. Rotational drive assembly 326 includes a rotational drive mechanism, shown as guide wire rotational drive mechanism 380, a cover 384, and a journal 388. Guide wire rotational drive mechanism 380 includes a chassis 382 and an engagement structure 386. Rotational drive assembly 326 is configured to cause guide wire 301 to rotate about its longitudinal axis. Engagement structure 386 is configured to releasably engage guide wire 301 and to apply sufficient force to guide wire 301 such that guide wire 301 is allowed to rotate about its longitudinal axis while permitting guide wire 301 to be moved axially by guide wire axial drive mechanism 350.

In the embodiment shown, rotational drive assembly 326 is supported within housing 316 such that rotation drive assembly 326 is permitted to rotate within housing 316. Engagement structure 386 applies sufficient force to guide wire 301 that the rotation of rotation drive assembly 326 causes guide wire 301 to rotate about its longitudinal axis as rotational drive assembly 326 rotates.

Chassis 382 includes a guide wire channel 390. Guide wire channel 390 is positioned generally perpendicular to the top surface of chassis 382 and runs the length of chassis 382 in the longitudinal direction. A plurality of tabs 392 extend vertically from the top surface of chassis 382 along guide wire channel 390. In FIG. 17, cover 384 is shown in the open position. Cover 384 is mounted to chassis 382 via hinge 394. Cassette 300 includes a restraint structure that acts to restrain movement of the guide wire when cover 384 is in the closed position. As shown, the restraint structure includes a plurality of tabs 396 extending from the lower surface of cover 384. The top surface of chassis 382 includes a plurality of recesses 398 configured to receive tabs 396 when cover 384 is in the closed position. Tabs 396 are positioned such that when cover 384 is closed, tabs 396 are positioned over guide wire channel 390 such that tabs 396 prevent guide wire 301 from falling out of guide wire channel 390 (i.e., restrains movement of the guide wire in a direction perpendicular to the top surface of chassis 382). In addition, the sidewalls of guide wire channel 390 and the engagement surfaces of wheels 522 and 524 prevent or restrain movement of guide wire 301 in other directions perpendicular to the longitudinal axis of guide wire 301. Thus, tabs 392 and guide wire channel 390 hold guide wire 301 within channel 390 during rotation of rotational drive assembly 326.

When cover 384 is in the open position, guide wire channel 390 is exposed allowing the user to load cassette 300 with a guide wire. With cover 384 open, guide wire 301 is loaded into rotational drive assembly 326 by placing the guide wire into guide wire channel 390. Tabs 392 facilitate the placement of guide wire 301 by aiding the user in aligning the guide wire with guide wire channel 390. As will be described in more detail below, once guide wire 301 is positioned within guide wire channel 390 engagement surfaces of engagement structure 386 are brought into engagement with the guide wire. In one embodiment, when the user activates controls (e.g., controls located at workstation 14) to open cover 384, rotational drive assembly 326 is automatically rotated such that guide wire channel 390 is facing generally upward to allow for easy loading or removal of guide wire 301.

In one embodiment, cassette 300 is a modular cassette that allows various components of cassette 300 to be removed and/or switched out with other components. In an exemplary embodiment, a user may wish to control the guide wire using bedside system 12 and to control the working catheter manually. In this embodiment, a user may mount only guide wire axial drive mechanism 350 and rotational drive assembly 326 within housing 316 of cassette 300. In another exemplary embodiment, a user may wish to control the working catheter using bedside system 12 and to control the guide wire manually. In this embodiment, a user may mount only working catheter drive mechanism 352 within housing 316 of cassette 300. In another embodiment, cassette 300 may include additional locations for mounting drive mechanisms for any type of additional catheter devices that may be used during a procedure. For example, a user may be able to couple drive mechanisms to cassette 300 to control the movement and/or control of an intravascular ultrasound catheter.

Figure 18:
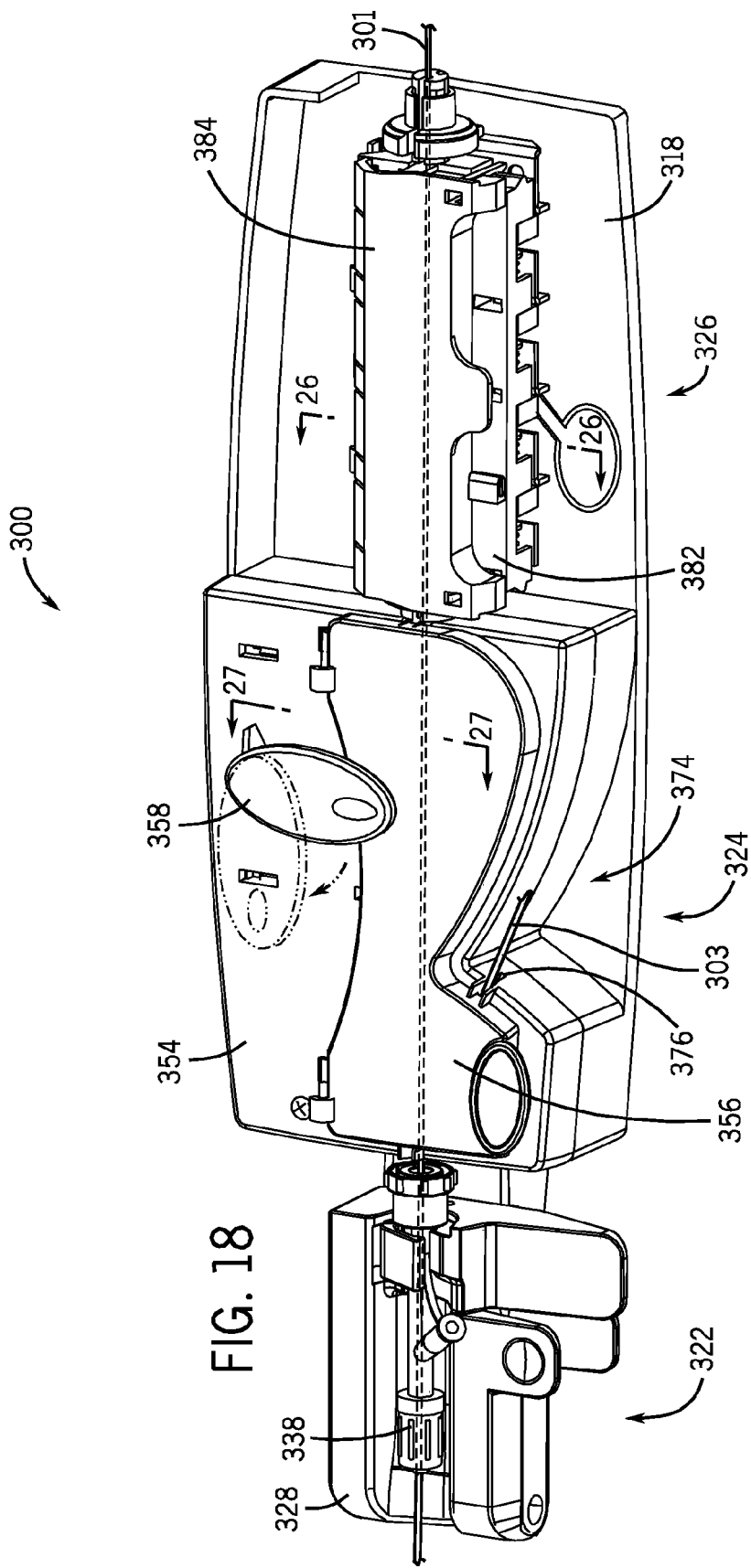
FIG. 18 is a perspective view of a cassette in the "loaded" or "use" configuration.

Referring to FIG. 18, cassette 300 is shown in the "loaded" or "use" position. In the "loaded" position, y-connector support assembly 322 is rotated downward such that y-connector 338 is aligned with guide wire channel 364 of axial drive assembly 324. The axial alignment allows guide wire 301 and working catheter 303 to be moved into and/or out of y-connector 338 via operation of guide wire axial drive mechanism 350 and working catheter axial drive mechanism 352. Cover 356 is shown in the closed position overlying both the guide wire axial drive mechanism 350 and the working catheter axial drive mechanism 352. As shown, cover 356 also covers guide wire channel 364 and working catheter channel 366. As such, cover 356 acts to prevent interference with the various components of axial drive assembly 324 during use.

After cover 356 is moved to the closed position, handle 358 is rotated approximately 90 degrees such that a portion of handle 358 is positioned over cover 356. As will be discussed in greater detail below, rotation of handle 358 to the closed position shown in FIG. 18 causes the engagement surface of the guide wire axial drive mechanism 350 and of the working catheter axial drive mechanism 352 to move together engaging the guide wire and working catheter, respectively.

In addition, when cassette 300 is moved to the "loaded" position, cover 384 is moved to the closed position overlying rotational drive mechanism 380 and guide wire channel 390 as shown in FIG. 18. Like cover 356, cover 384 acts to prevent interference with the various components of rotational drive assembly 326 during use. In one embodiment, a user may activate controls (e.g., controls located at workstation 14) to cause the various components of cassette 300 to move between the "loading" and "loaded" positions. In addition, cassette 300 may also be configured to allow the user to move the various components of cassette 300 between the "loading" and "loaded" positions manually.

Referring to FIG. 18, in the "loaded" or "use" configuration, the longitudinal axis (and the internal lumen) of y-connector 338 is aligned with guide wire channel 364 of axial drive assembly and with guide wire channel 390 of rotational drive assembly 326. This alignment provides a path extending from the rear of cassette 300 through y-connector 338 into the guide catheter through which the guide wire is advanced or retracted during axial movement of the guide wire. In various embodiments, components of cassette 300, including top deck 354, chassis 382, cover 356, and cover 384, may be made from a transparent or translucent plastic.

Figure 19:
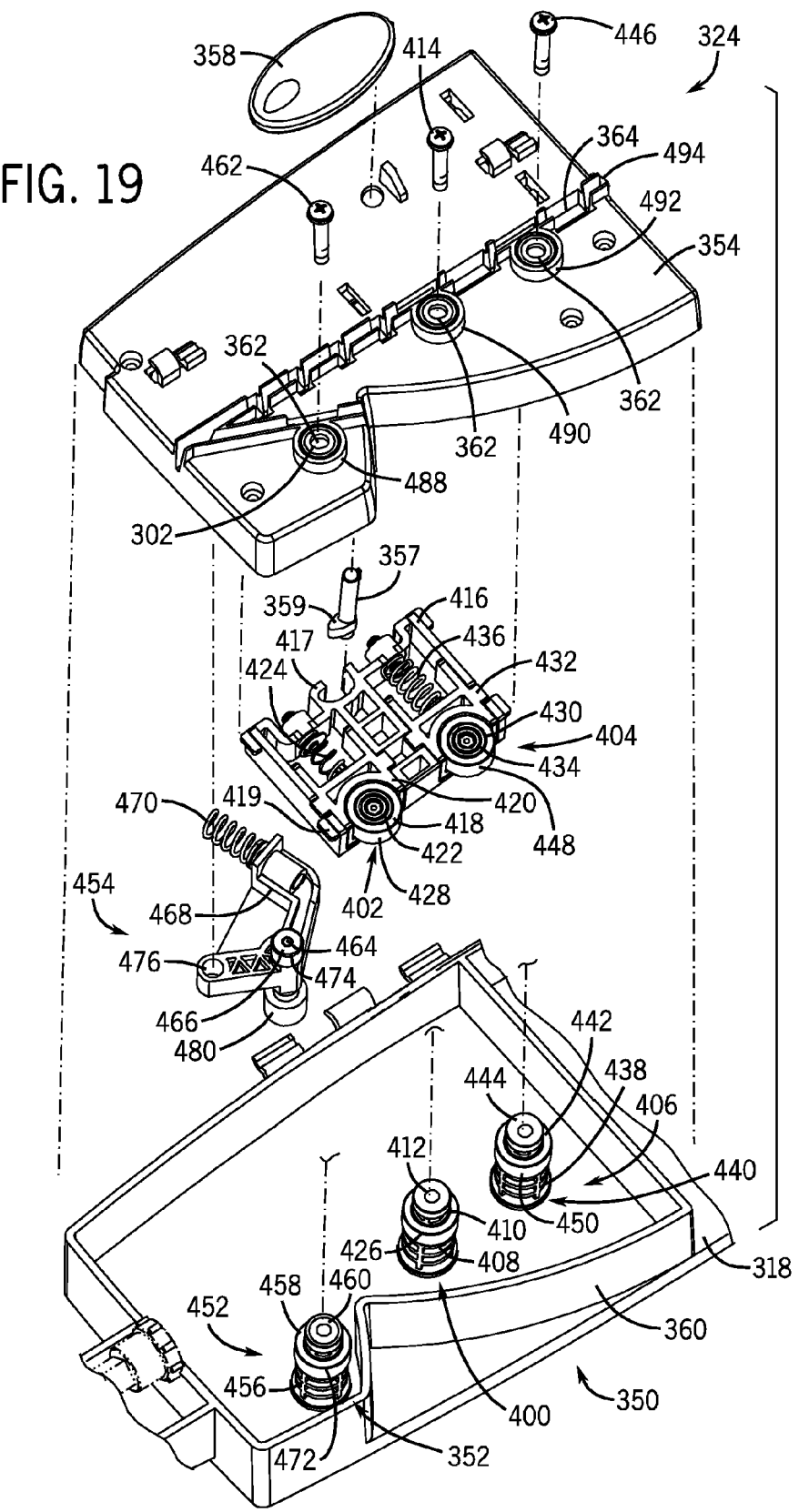
FIG. 19 is an exploded perspective view of an axial drive assembly of a cassette.

Referring to FIG. 19, an exploded perspective view from above of axial drive assembly 324 is shown. FIG. 19 generally depicts the components of axial drive assembly 324. Guide wire axial drive mechanism 350 and working catheter axial drive mechanism 352 are positioned above base plate 318 and top deck 354 is fastened to central portion 360 of base plate 318 above guide wire axial drive mechanism 350 and working catheter axial drive mechanism 352. Thus, guide wire axial drive mechanism 350 and working catheter axial drive mechanism 352 are generally enclosed within a chamber defined by top deck 354 and central portion 360 of base plate 318 when axial drive assembly 324 is assembled. Top deck 354 includes a plurality of apertures 362 to receive various portions of both axial drive mechanism 350 and working catheter axial drive mechanism 352.

Axial drive mechanism 350 includes a drive element 400, a first roller assembly 402, a second roller assembly 404, and a guide wire axial motion sensor assembly, shown as encoder assembly 406. First roller assembly 402 and second roller assembly 404 are both mounted within a housing 416. Drive element 400 includes a drive shaft 408, a drive wheel 410, a bearing 412, and a screw 414. Drive shaft 408 is configured to engage second capstan 306 of motor drive base 302 such that drive shaft 408 and drive wheel 410 rotate in response to rotation of second capstan 306. First roller assembly 402 includes an idler wheel or roller 418, a wheel housing 420, a bearing 422, and a spring 424.

Drive wheel 410 includes an outer or engagement surface 426, and roller 418 includes an outer or engagement surface 428. Generally, when guide wire axial drive mechanism 350 is placed in the "use" or "engaged" position (shown in FIG. 22), guide wire 301 is positioned between drive wheel 410 and roller 418 such that engagement surface 426 of drive wheel 410 and engagement surface 428 of roller 418 are able to engage the guide wire. In this embodiment, engagement surface 426 and engagement surface 428 define a pair of engagement surfaces. The force applied to guide wire 301 by engagement surface 426 and engagement surface 428 is such that drive wheel 410 is able to impart axial motion to guide wire 301 in response to the rotation of drive shaft 408 caused by rotation of second capstan 306. This axial motion allows a user to advance and/or retract a guide wire via manipulation of controls located at workstation 14. Roller 418 is rotatably mounted within wheel housing 420 and rotates freely as drive wheel 410 rotates to drive guide wire 301. Spring 424 is biased to exert a force onto wheel housing 420 causing roller 418 to engage the guide wire against drive wheel 410. Spring 424 is selected, tuned, and/or adjusted such that the proper amount of force is applied to guide wire 301 by engagement surface 426 and engagement surface 428 in the "engaged" position. In other embodiments, additional drive elements may be added as necessary to impart axial motion to the guide wire.

Second roller assembly 404 includes an idler wheel or roller 430, a wheel housing 432, a bearing 434, and a spring 436. Encoder assembly 406 includes shaft 438, magnetic coupling 440, idler wheel or roller 442, bearing 444, and a screw 446. Roller 430 includes an outer or engagement surface 448 and roller 442 includes an outer or engagement surface 450.

In the "engaged" position, guide wire 301 is positioned between roller 430 and roller 442 such that engagement surface 448 of roller 430 and engagement surface 450 of roller 442 are able to engage the guide wire. In this embodiment, engagement surface 448 and engagement surface 450 define a pair of engagement surfaces. The force applied to guide wire 301 by engagement surface 448 and engagement surface 450 is such that drive wheel 410 is able to pull guide wire 301 past roller 430 and 442. In this way, the pair of non-active or idle rollers 430 and 442 help support guide wire 301 and maintain alignment of guide wire 301 along the longitudinal axis of cassette 300.

Roller 430 is rotatably mounted within wheel housing 432, and roller 442 is rotatably mounted to shaft 438. Both rollers 430 and 442 are mounted to rotate freely as drive wheel 410 imparts axial motion to guide wire 301. Spring 436 is biased to exert a force onto wheel housing 432 causing roller 430 to engage guide wire 301 against roller 442. Spring 436 is selected, tuned, and/or adjusted such that the proper amount of force is applied to guide wire 301 by engagement surface 448 and engagement surface 450 in the "engaged" position to support the guide wire while still allowing the guide wire to be moved axially by drive wheel 410. In other embodiments, additional pairs of non-active or idler rollers may be added as needed to provide proper support and alignment for the guide wire. In one embodiment, spring 424 and spring 436 are selected or adjusted such that the force applied to guide wire 301 by wheels 430 and 442 is approximately the same as the force applied to guide wire 301 by wheels 410 and 418.

Encoder assembly 406 includes magnetic coupling 440 that engages a magnetic encoder located within motor drive base 302. The magnetic encoder is configured to measure an aspect (e.g., speed, position, acceleration, etc.) of axial movement of the guide wire. As roller 442 rotates, shaft 438 rotates causing magnetic coupling 440 to rotate. The rotation of magnetic coupling 440 causes rotation of the magnetic encoder within motor drive base 302. Because rotation of roller 442 is related to the axial movement of guide wire 301, the magnetic encoder within motor drive base 302 is able to provide a measurement of the amount of axial movement experienced by guide wire 301 during a procedure. This information may be used for a variety of purposes. For example, this information may be displayed to a user at workstation 14, may be used in a calculation of or estimated position of the guide wire within the vascular system of a patient, may trigger an alert or alarm indicating a problem with guide wire advancement, etc.

As shown in FIG. 19, first roller assembly 402 and second roller assembly 404 are both mounted within a housing 416. Housing 416 provides a common support for first roller assembly 402 and second roller assembly 404. As will be discussed in more detail below, first roller assembly 402 and second roller assembly 404 are moved away from drive wheel 410 and roller 442, respectively, when axial drive assembly 324 is placed in the "loading" configuration. This facilitates placement of guide wire 301 between the opposing pairs of engagement surfaces of guide wire axial drive mechanism 350. Housing 416 allows first roller assembly 402 and second roller assembly 404 to be moved together (e.g., in sync) away from drive wheel 410 and roller 442, respectively, when axial drive assembly 324 is placed in the "load" configuration.

Axial drive assembly 324 also includes working catheter axial drive mechanism 352. Working catheter axial drive mechanism 352 includes a drive element 452 and a working catheter axial motion sensor assembly, shown as working catheter encoder assembly 454. Drive element 452 includes a drive shaft 456, a drive wheel 458, a bearing 460, and a screw 462. Drive shaft 456 is configured to engage first capstan 304 of motor drive base 302 such that drive shaft 456 and drive wheel 458 rotate in response to rotation of first capstan 304. Encoder assembly 454 includes shaft 464, a roller 466, an encoder linkage 468, a spring 470, and a magnetic coupling 480.

Drive wheel 458 includes an outer or engagement surface 472 and roller 466 includes an outer or engagement surface 474. When working catheter axial drive mechanism 352 is in the "engaged" position, a working catheter is positioned between drive wheel 458 and roller 466, such that engagement surface 472 and engagement surface 474 are able to engage working catheter 303. In this embodiment, engagement surfaces 472 and 474 define a pair of engagement surfaces. The force applied to working catheter 303 by engagement surfaces 472 and 474 is such that drive wheel 458 is able to impart axial motion to the working catheter in response to the rotation of drive shaft 456 caused by rotation of first capstan 304. This axial motion allows a user to advance and/or retract a working catheter via manipulation of controls located at workstation 14. Roller 466 is rotatably mounted to shaft 464 and rotates freely as drive wheel 458 rotates to drive the working catheter.

Spring 470 is coupled to a first end of linkage 468. The second end of linkage 468 includes an aperture 476 that is pivotally coupled to a post 478 extending from the inner surface of top deck 354. Spring 470 is biased to exert a force on to linkage 468 causing linkage 468 to pivot about post 478 to force roller 466 to engage working catheter 303 against drive wheel 458. Spring 470 is selected, tuned, and/or adjusted such that the proper amount of force is applied to working catheter 303 by engagement surfaces 472 and 474 in the "engaged" position to allow drive wheel 458 to impart axial movement to the working catheter.

Encoder assembly 454 includes magnetic coupling 480 that engages a magnetic encoder located within motor drive base 302. The magnetic encoder is configured to measure an aspect (e.g., speed, position, acceleration, etc.) of axial movement of the working catheter. As roller 466 rotates, shaft 464 rotates causing magnetic coupling 480 to rotate. The rotation of magnetic coupling 480 causes rotation of the magnetic encoder within motor drive base 302. Because rotation of roller 466 is related to the axial movement of working catheter 303, the magnetic encoder within motor drive base 302 is able to provide a measurement of the amount of axial movement experienced by the working catheter during a procedure. This information may be used for a variety of purposes. For example, this information may be displayed to a user at workstation 14, may be used in a calculation of or estimated position of the working catheter within the vascular system of a patient, may trigger an alert or alarm indicating a problem with working catheter advancement, etc.

As will be discussed in more detail below, roller 466 is moved away from drive wheel 458 when axial drive assembly 324 is placed in the "loading" configuration. This facilitates placement of the working catheter between the opposing pairs of engagement surfaces of working catheter axial drive mechanism 352.

In one embodiment, cassette 300 and/or motor drive base 302 includes a locking mechanism that is configured to lock the position of guide wire 301 during manipulation of the working catheter 303 and to lock the position of working catheter 303 during manipulation of guide wire 301. In one embodiment, the locking mechanism acts to increase the force applied to the guide wire by the engagement surfaces when the working catheter is being advanced and to increase the force applied to the working catheter by the engagement surfaces when the guide wire is being advanced.

Figure 20:
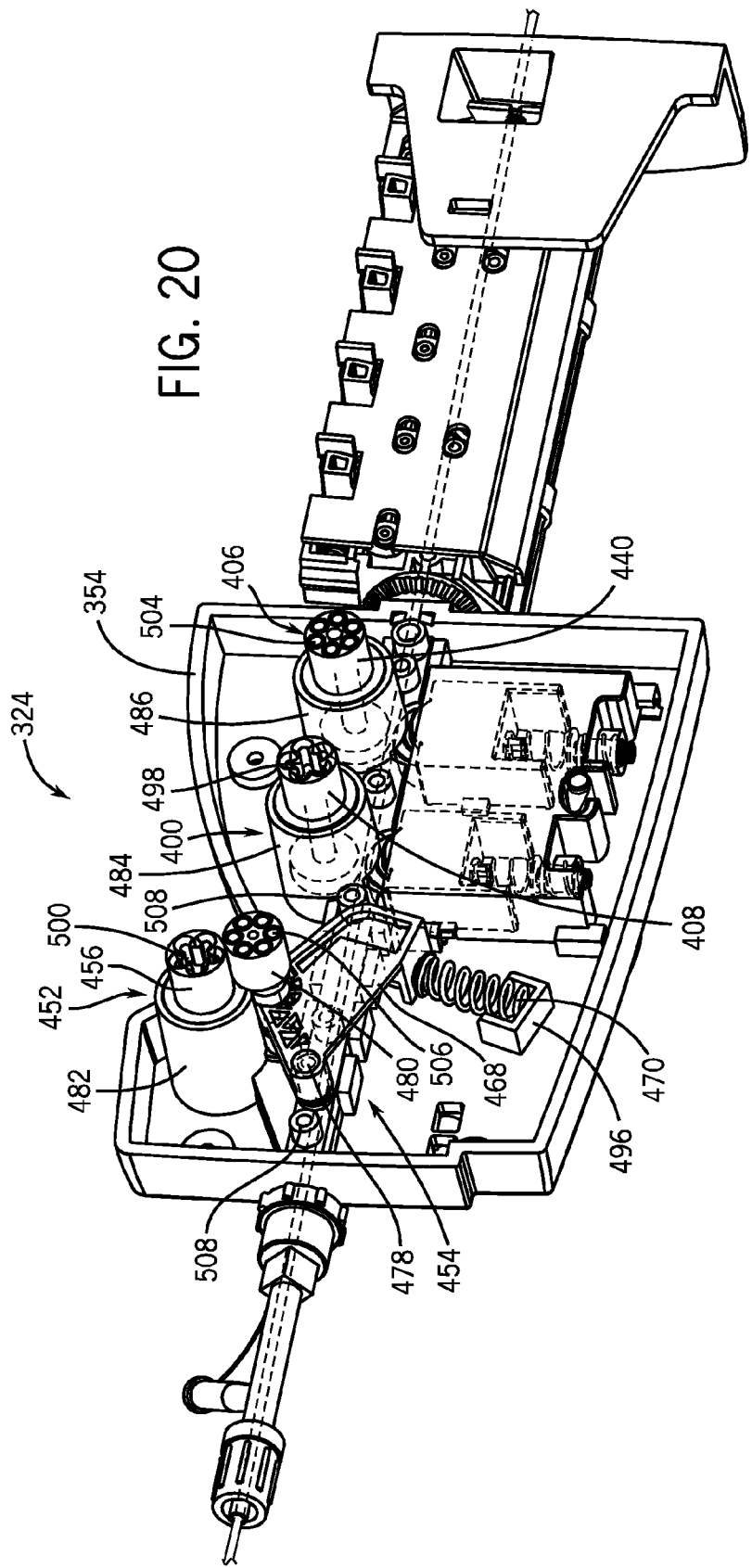
FIG. 20 is a bottom perspective view of a cassette showing the base plate removed.

Referring to FIGS. 19 and 20, top deck 354 includes a plurality of cylindrical sleeves, first sleeve 482, second sleeve 484, and third sleeve 486, extending from the inner or lower surface of top deck 354. Top deck 354 also includes a plurality of cylindrical collars, first collar 488, second collar 490, and third collar 492, extending from the upper surface of top deck 354. Collar 488 is in axial alignment with sleeve 482. Collar 490 is in axial alignment with sleeve 484. Collar 492 is in axial alignment with sleeve 486. Each of the collars 488, 490, and 492 define an aperture 362. In the embodiment shown, sleeve 482 and collar 488 are configured to receive working catheter drive element 452, sleeve 484 and collar 490 are configured to receive guide wire drive element 400, and sleeve 486 and collar 492 are configured to receive guide wire encoder assembly 406. Apertures 362 provide access to screws 414, 446, and 462 once top deck 354 is mounted over axial drive assembly 324.

Top deck 354 includes a collar 494 aligned with and located at the back end of guide wire channel 364. Collar 494 is configured to receive front shaft 512 that extends from chassis 382 of rotational drive assembly 326. Collar 494 is configured to allow front shaft 512 (and consequently the rest of rotational drive assembly 326) to rotate about the longitudinal axis of guide wire channel 390 relative to axial drive assembly 324. In one embodiment, rotational drive assembly 326 is able to rotate relative to housing 316 of cassette 300 while axial drive assembly 324 does not rotate relative to housing 316. In another embodiment, both rotational drive assembly 326 and axial drive assembly 324 rotate relative to housing 316 of cassette 300.

FIG. 20 is a bottom perspective view of cassette 300 showing top deck 354 mounted above guide wire axial drive mechanism 350 and working catheter axial drive mechanism 352. FIG. 20 shows working catheter drive element 452, guide wire drive element 400, and guide wire encoder assembly 406 received within sleeves 482, 484, and 486. A support structure 496 extends from the lower surface of top deck 354. Spring 470 is coupled at one end to support structure 496 allowing spring 470 to compress and expanded between linkage 468 and support structure 496.

As shown, the lower end of drive shaft 408 includes a keyed recess 498, and the lower end of drive shaft 456 includes a keyed recess 500. Keyed recess 500 is one embodiment of first capstan socket 310, and keyed recess 498 is one embodiment of second capstan socket 312. Keyed recess 500 is configured to receive a capstan, such as first capstan 304, and keyed recess 498 is configured to receive a capstan, such as second capstan 306. First capstan 304 and second capstan 306 are keyed to fit within keyed recess 500 and 498 and to engage and turn drive shafts 456 and 408 upon rotation of the capstans.

As shown, magnetic coupling 440 of guide wire encoder assembly 406 includes a circular array of magnets 504. Magnetic coupling 480 of working catheter encoder assembly 454 includes a circular array of magnets 506. Magnetic couplings 440 and 480 engage with magnetic encoders positioned within motor drive base 302. The magnetic encoders of motor drive base 302 are coupled to appropriate electronics to detect and measure rotation of rollers 442 and 466 and to calculate axial motion of guide wire 301 and working catheter 303 based on the measured rotations. While this embodiment discloses the use of magnetic encoders to detect the axial motion of the guide wire and working catheter, other sensors may be used. In one embodiment, axial motion of the guide wire may be detected by an optical sensor that detects movement of the guide wire and/or working catheter by scanning the surface of the guide wire and/or working catheter as it passes the optical sensor. In one such embodiment, the optical sensor includes an LED light source and a detector (e.g., a complimentary metal oxide semiconductor, other light detecting circuitry, etc.) that detects light reflected off the surface of the guide wire and/or working catheter, and the light detected by the detector is analyzed (e.g., by a digital signal processor) to determine movement of the guide wire and/or working catheter. In another embodiment, the surface of the guide wire and/or working catheter may include indicia that are detected to determine axial movement of the guide wire. In other embodiments, other types of sensors (e.g., resolvers, sychros, potentiometers, etc.), may be used to detect movement of the guide wire and/or working catheter.

Cassette 300 also includes a series of magnets 508 positioned below guide wire channel 364. Because, in at least some embodiments, the guide wire is made from a magnetic material, magnets 508 are able to interact with the guide wire. In this embodiment, the magnetic attraction created by magnets 508 helps the user position guide wire 301 during loading by drawing guide wire 301 into guide wire channel 364. The magnetic attraction created by magnets 508 also tends to hold guide wire 301 within guide wire channel 364 during advancement and/or retraction of the guide wire. Further, magnets 508 help to hold guide wire 301 straight (i.e., parallel to the longitudinal axis of guide wire channel 364) to aid in the axial movement caused by guide wire axial drive mechanism 350.

Figure 21:
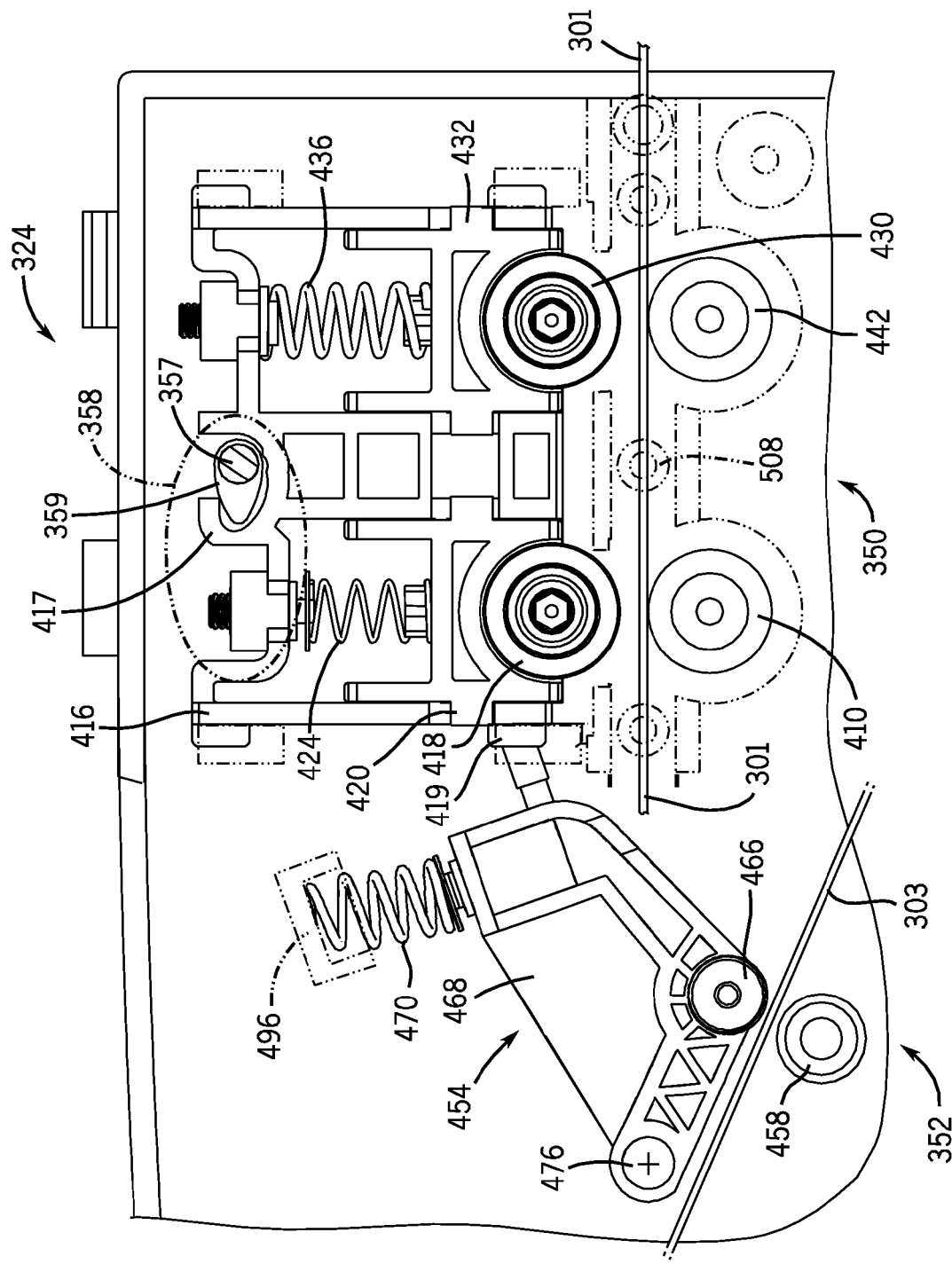
FIG. 21 is a top view showing the axial drive assembly in the "disengaged" position.
Figure 22:
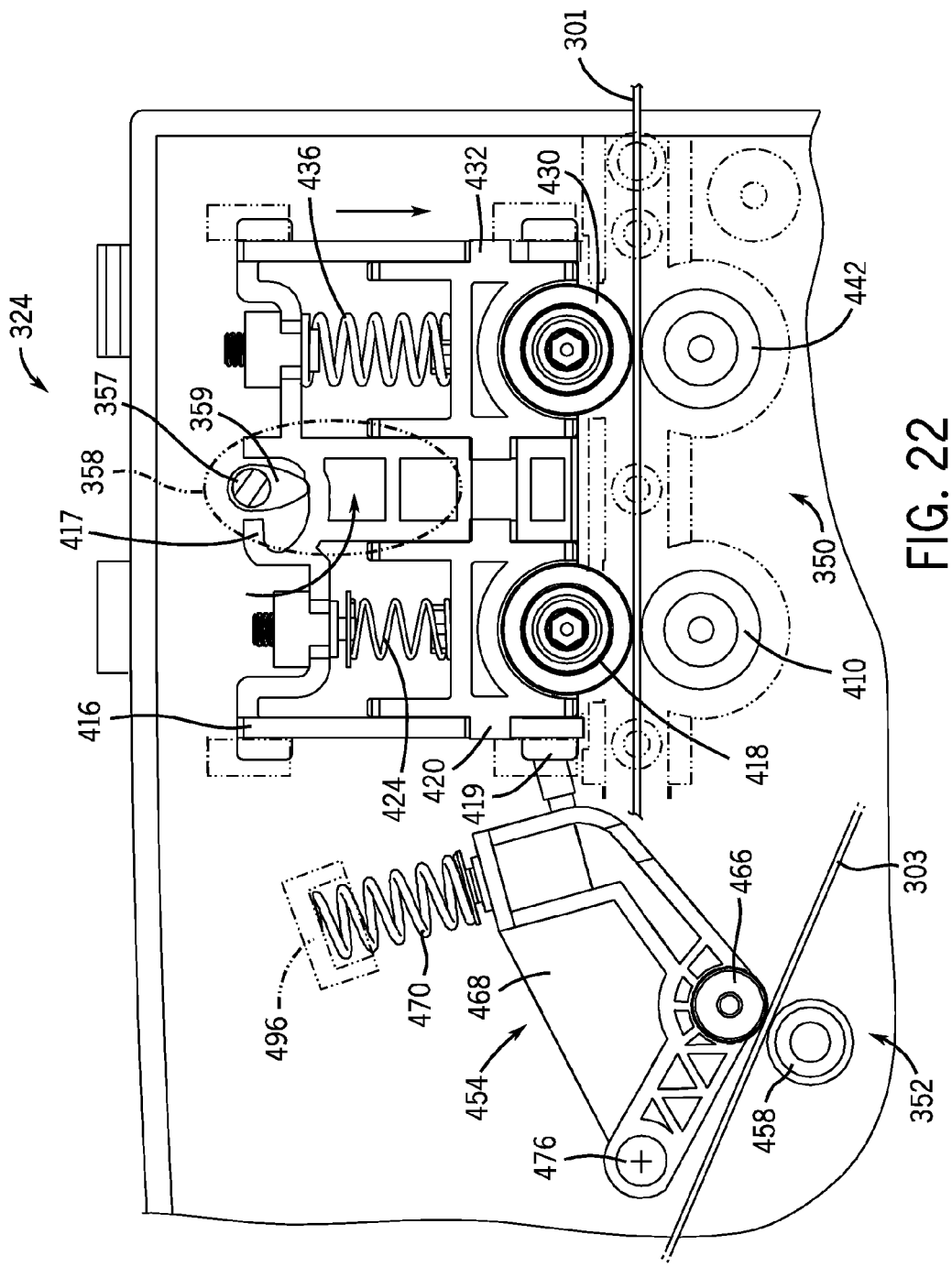
FIG. 22 is a top view showing the axial drive assembly in the "engaged" position.

FIG. 21 shows a top view of axial drive assembly 324 in the "loading" configuration with handle 358 (shown in broken lines) rotated such that it is generally parallel to guide wire channel 364. FIG. 22 shows a top view of axial drive assembly 324 in the "loaded" or "use" configuration with handle 358 rotated such that it is generally perpendicular to guide wire channel 364. Generally, when handle 358 is moved from the position of FIG. 22 to the position of FIG. 21, the engagement surfaces of both guide wire axial drive mechanism 350 and working catheter axial drive mechanism 352 are moved away from each other increasing the space between the pairs of wheels in the drive mechanisms. This provides sufficient space between the wheels of each drive mechanism to allow the user to place guide wire 301 and working catheter 303 into the channels between the wheels. Generally, as handle 358 is moved from the position of FIG. 21 to the position of FIG. 22, the engagement surfaces of both guide wire axial drive mechanism 350 and working catheter axial drive mechanism 352 are moved toward each other bringing the engagement surfaces of each drive mechanism into engagement with guide wire 301 or working catheter, respectively.

In the embodiment shown, handle 358 is coupled to a shaft 357. Shaft 357 includes a cam section 359 and housing 416 includes a cam surface 417. As handle 358 rotates from the position shown in FIG. 21 to the position shown in FIG. 22, cam section 359 of shaft 357 moves along cam surface 417 causing housing 416 to move toward guide wire 301. This motion engages guide wire 301 between drive wheel 410 and roller 418 and between roller 430 and roller 442. When handle 358 is brought into the position of FIG. 22, springs 424 and 436 are compressed to the proper tension to allow drive wheel 410 to move guide wire 301 axial along its longitudinal axis.

In addition, housing 416 includes a tab 419 that is coupled to linkage 468. Thus, linkage 468 rotates about post 478 when housing 416 is moved to the position shown in FIG. 21. This movement draws roller 466 away from working catheter drive wheel 458. When, housing 416 is moved to the position shown in FIG. 22, roller 466 is moved toward catheter drive wheel 458 such that the engagement surfaces of roller 466 and drive wheel 458 engage working catheter 303. In one embodiment, cassette 300 is configured to allow the user to move the axial drive assembly 324 between the "use" and "loading" positions via manipulation of controls at workstation 14. Cassette 300 may also be configured to allow the user to move the axial drive assembly 324 between the "use" and "loading" position manually.

Figure 23A:
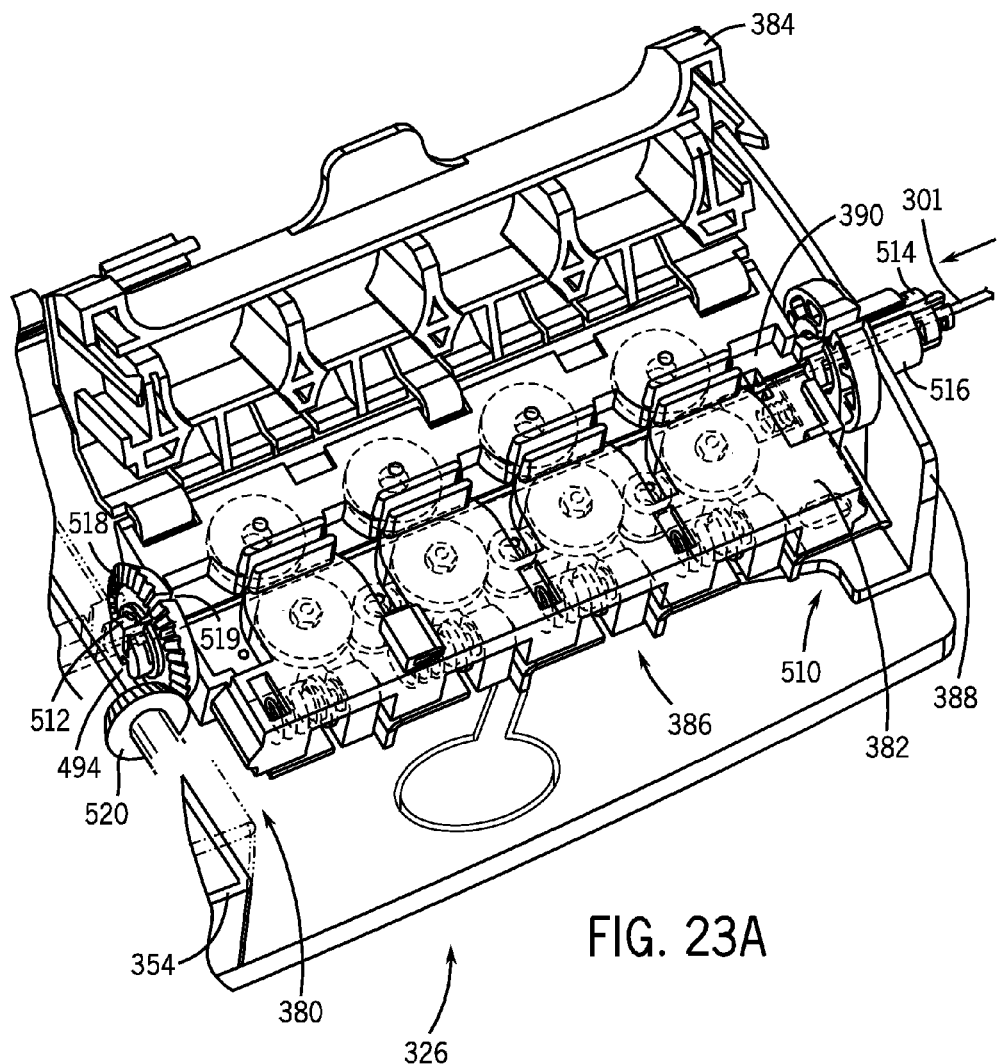
FIG. 23A is a top perspective view of a rotational drive assembly of a cassette showing the engagement structure in broken lines beneath the chassis.
Figure 23B:
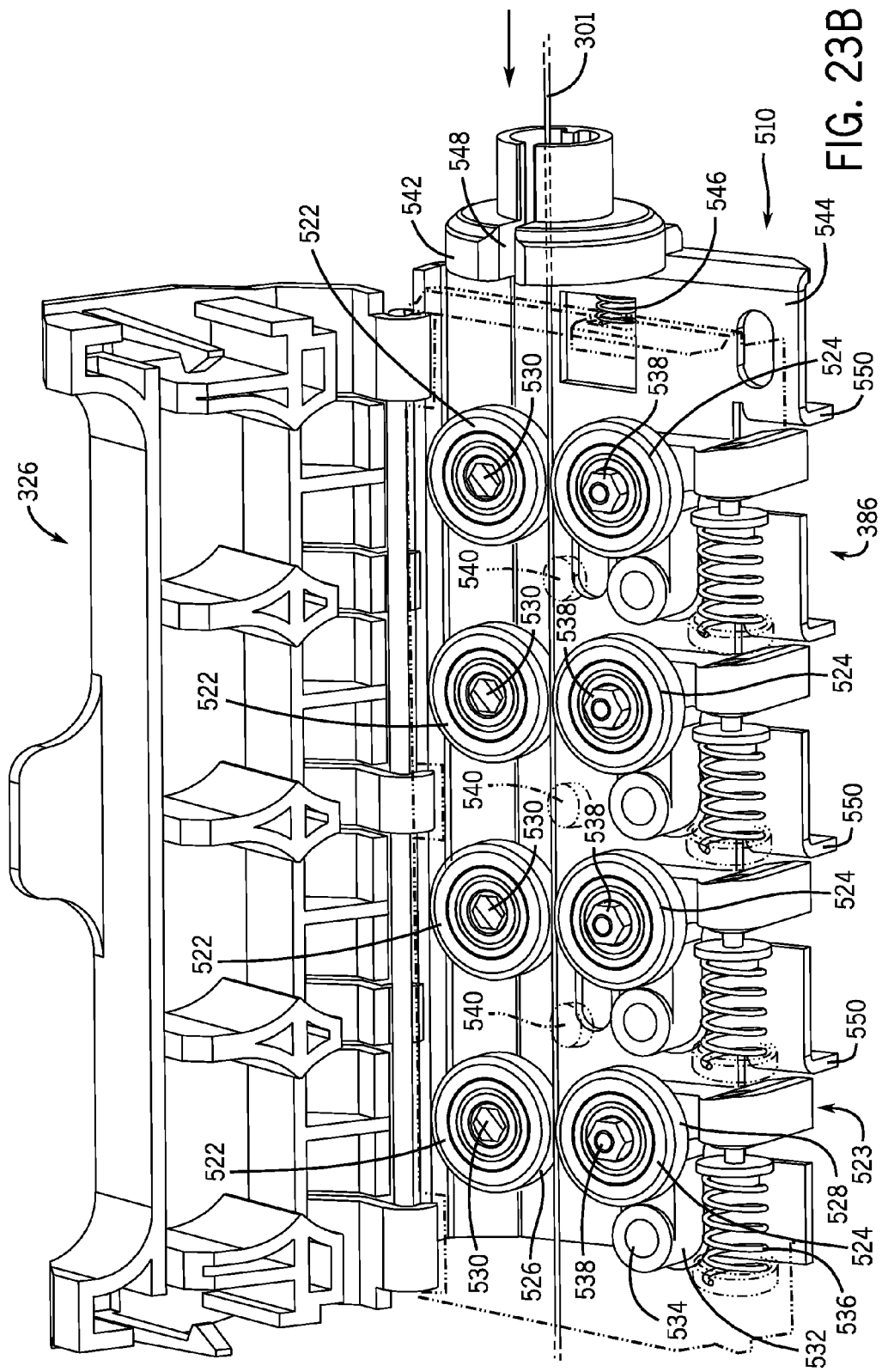
FIG. 23B is a top perspective view of a rotational drive assembly with the chassis shown in broken lines.

FIGS. 23A and 23B show a perspective view of rotational drive assembly 326 showing cover 384 in the open position. Rotational drive assembly 326 includes rotational drive mechanism 380, chassis 382, an engagement structure 386, and a disengagement assembly 510. Chassis 382 fits over engagement structure 386 and provides mounting for various components of rotational drive assembly 326. Chassis 382 includes a front shaft 512 and a rear shaft 514. As discussed above, front shaft 512 is rotatably received within collar 494 of top deck 354, and rear shaft 514 is rotatably received within collar 516 such that rotational drive mechanism 380 is able to rotate relative to journal 388. As shown, collar 516 extends through and is supported by journal 388 such that rear shaft 514 rotates within collar 516 as rotational drive mechanism 380 is rotated. Collar 516 rests within a recess or slot formed within journal 388. In another embodiment, rear shaft 514 may be in direct contact with journal 388 such that rear shaft 514 rotates within the recess or slot of journal 388 as rotational drive mechanism 380 is rotated. Guide wire channel 390 extends the length of chassis 382 through both front shaft 512 and rear shaft 514.

Rotational drive mechanism 380 includes rotation bevel gear 518 that engages a drive gear 520. Bevel gear 518 is rigidly coupled to front shaft 512 of chassis 382 such that rotation of bevel gear 518 rotates chassis 382. Drive gear 520 is coupled to a rotational actuator positioned in motor drive base 302 and engages bevel gear 518. Rotation of the rotational actuator in motor drive base 302 causes drive gear 520 to rotate which causes bevel gear 518 to rotate which in turn causes rotational drive mechanism 380 to rotate. Rotational drive mechanism 380 is allowed to rotate about the longitudinal axis of guide wire channel 390 via the rotatable connections between front shaft 512 and top deck 354 and between rear shaft 514 and journal 388. Bevel gear 518 further includes a slot 519 in axial alignment with guide wire channel 390. Slot 519 allows the user to place guide wire 301 into guide wire channel 390 by dropping it in vertically as opposed to threading it through bevel gear 518. In one embodiment, rotational drive assembly 326 is equipped with one or more sensors that are configured to measure an aspect (e.g., speed, position, acceleration, etc.) of rotation of the guide wire and/or any other structure of rotational drive assembly 326. The sensors that measure rotation of the guide wire may include magnetic encoders and/or optical sensors as discussed above regarding the sensors that measure axial motion of the guide wire and/or working catheter. However, any suitable sensor (e.g., resolvers, sychros, potentiometers, etc.) may be used to detect rotation of the guide wire.

Referring to FIG. 23B, engagement structure 386 is shown according to an exemplary embodiment. As shown, engagement structure 386 includes four pairs of idler wheels or rollers. Each pair of rollers includes a fixed wheel 522 and an engagement wheel 524. Fixed wheels 522 are rotatably coupled to chassis 382 via fixation posts 530. Each engagement wheel 524 is part of an engagement wheel assembly 523. Each engagement wheel assembly 523 includes a pivot yoke 532 and a spring 536. Each engagement wheel is mounted to pivot yoke 532 via a mounting post 538. Each pivot yoke 532 is pivotally coupled to chassis 382 via fixation posts 534.

Each fixed wheel 522 includes an outer or engagement surface 526 and each engagement wheel 524 includes an outer or engagement surface 528. Generally, FIG. 23B shows engagement structure 386 in the "use" or "engaged" position. In the "engaged" position, guide wire 301 is positioned between fixed wheels 522 and engagement wheels 524 such that engagement surfaces 526 and 528 are able to engage guide wire 301. In this embodiment, engagement surface 526 and engagement surface 528 of each pair of rollers define a pair of engagement surfaces. The force applied to guide wire 301 by engagement surfaces 526 and 528 is sufficient to cause the guide wire to rotate about its longitudinal axis as rotational drive assembly 326 is rotated. Further, the force applied to guide wire 301 by engagement surfaces 526 and 528 is also sufficient to allow the guide wire to be moved axially by guide wire axial drive mechanism 350.

Springs 536 are biased to exert a force onto pivot yokes 532 causing each engagement wheel 524 to engage the opposite fixed wheel 522. The generally L-shape of pivot yoke 532 allows springs 536 to be aligned with the longitudinal axis of guide wire 301 and still cause engagement between engagement wheels 524, fixed wheels 522, and the guide wire. This allows the lateral dimension of rotational drive assembly 326 to be less than if springs 536 were positioned perpendicular to the longitudinal axis of the guide wire. Springs 536 are selected, tuned, and/or adjusted such that the proper amount of force is applied to the guide wire by engagement surfaces 526 and 528 in the "engaged" position.

Cassette 300 also includes a series of magnets 540 located beneath guide wire channel 390. Because, in at least some embodiments the guide wire is made from a magnetic material, magnets 540 are able to interact with the guide wire. In this embodiment, the magnetic attraction created by magnets 540 helps the user position guide wire 301 during loading by drawing guide wire 301 into guide wire channel 390. The magnetic attraction created by magnets 540 also tends to hold guide wire 301 within guide wire channel 390 during advancement and/or retraction of the guide wire. Further, magnets 540 help to hold guide wire 301 straight (i.e., parallel to the longitudinal axis of guide wire channel 390) to aid in the axial movement caused by guide wire axial drive mechanism 350.

Rotational drive assembly also includes a disengagement assembly 510. Disengagement assembly 510 includes a stepped collar 542, a base plate 544, and a spring 546. Stepped collar 542 is coupled to base plate 544, and spring 546 is coupled at one end to chassis 382 and at the other end to base plate 544. Stepped collar 542 includes a slot 548 in axial alignment with guide wire channel 390. Like slot 519, slot 548 allows the user to place guide wire 301 into guide wire channel 390 by dropping it in vertically as opposed to threading it through stepped collar 542. Base plate 544 includes a plurality of engagement arms 550 that extend generally perpendicular to the plane defined by base plate 544.

Figure 24:
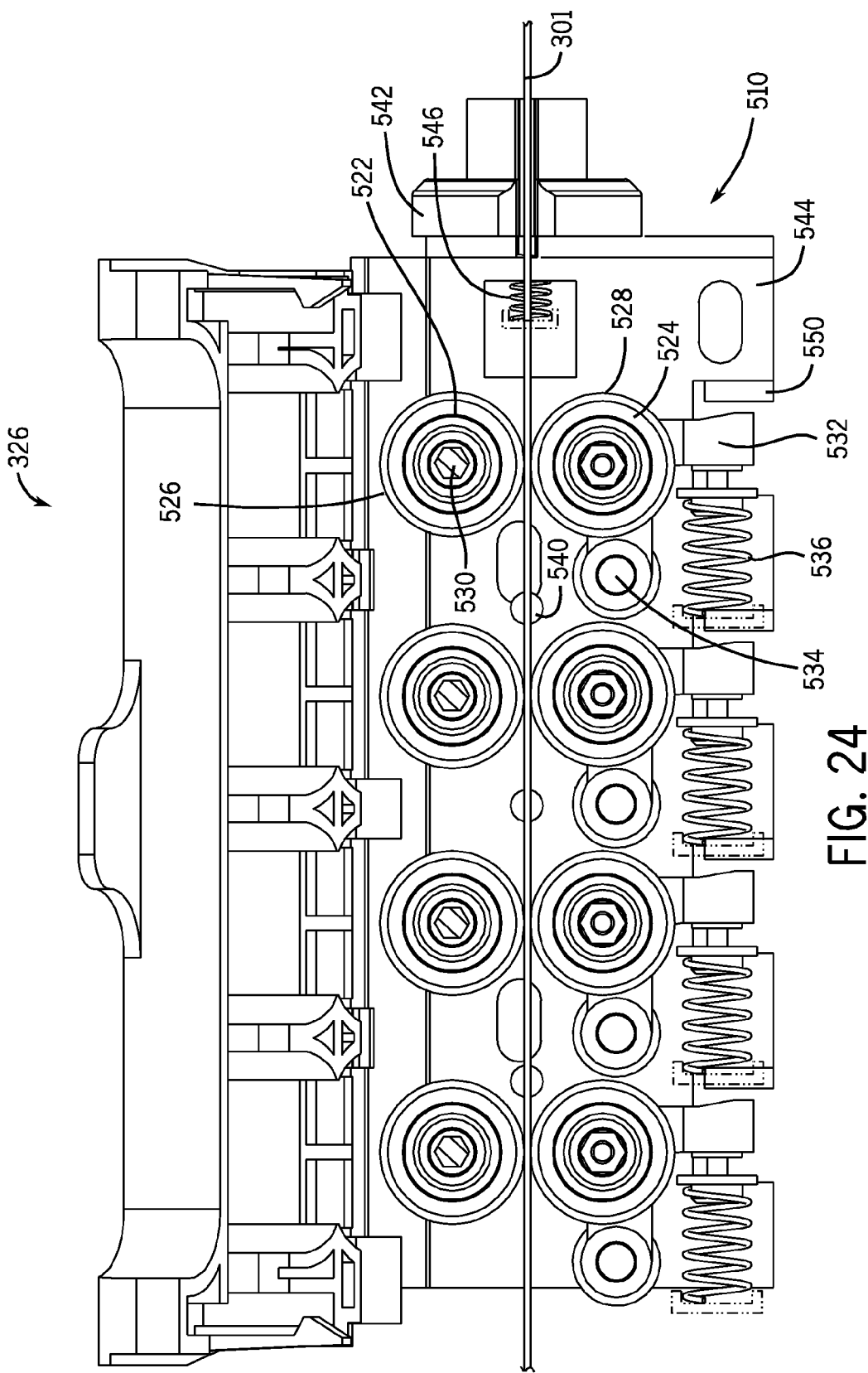
FIG. 24 is a top view of the rotational drive assembly in the "engaged" position.
Figure 25:
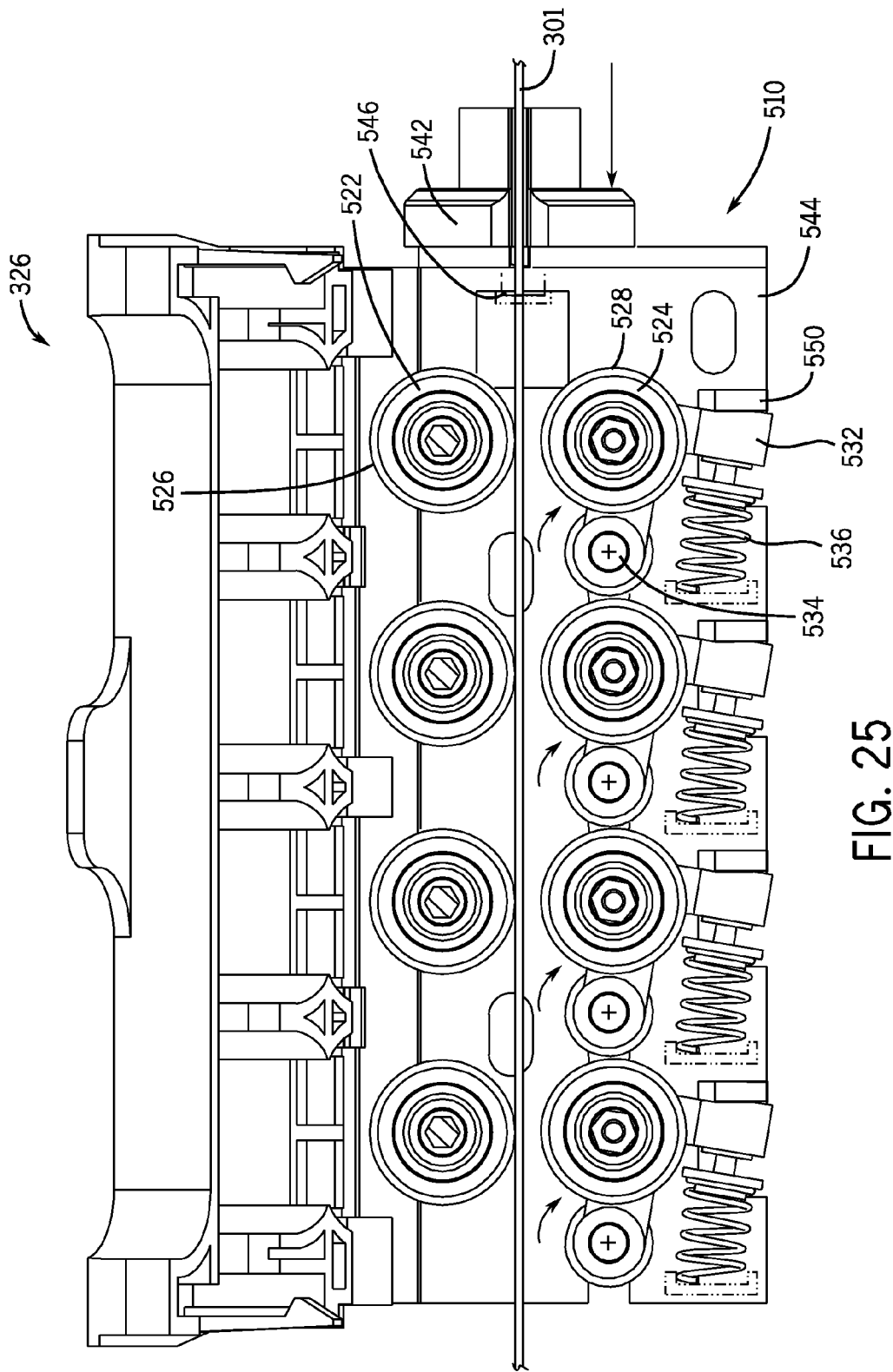
FIG. 25 is a top view of the rotational drive assembly in the "disengaged" position.

Generally, disengagement assembly 510 allows engagement wheels 524 to be moved away from fixed wheels 522. Referring to FIGS. 24 and 25, FIG. 25 shows a top view of rotational drive assembly 326 in the "loading" configuration, and FIG. 24 shows a top view of rotational drive assembly 326 in the "loaded" or "use" configuration. To cause engagement wheels 524 to disengage from guide wire 301, an axially directed force (depicted by the arrow in FIG. 25) is applied to stepped collar 542. This causes base plate 544 to move toward the front of cassette 300 in the direction of the arrow. As base plate 544 moves forward, spring 546 is compressed, and engagement arms 550 are brought into contact with pivot yokes 532. The contact between engagement arms 550 and pivot yokes 532 causes springs 536 to be compressed, and pivot yokes 532 pivot about fixation posts 534. As pivot yokes 532 pivot, engagement wheels 524 are drawn away from fixed wheels 522. As shown in FIG. 25, this provides sufficient space between engagement wheels 524 and fixed wheels 522 to allow the user to place guide wire 301 into guide wire channel 390.

When the axial force is removed from stepped collar 542, engagement wheels 524 move from the position shown in FIG. 25 to the "engaged" position shown in FIG. 24. When the axial force is removed, spring 546 and springs 536 are allowed to expand causing engagement arms 550 to disengage from pivot yokes 532. Pivot yokes 532 pivot counterclockwise about fixation posts 534, bringing engagement wheels 524 back toward guide wire channel 390 causing engagement surfaces 526 of fixed wheels 522 and engagement surfaces 528 of engagement wheels 524 to engage guide wire 301.

In one embodiment, a user may activate controls located at workstation 14 to cause rotational drive assembly 326 to move between the "use" position and the "loading" position. In this embodiment, rotational drive assembly 326 is automatically rotated such that guide wire channel 390 is facing generally upward to allow for easy loading or removal of the guide wire. In the embodiment shown, chassis 382 rotates relative to stepped collar 542. In this embodiment, when rotational drive assembly 326 is in the "loading" position, a path defined by the engagement surfaces of engagement structure 386 and guide wire channel 390 align with slot 548 of stepped collar 542. Motor drive base 302 may also include a structure (e.g., two rods, etc.) that applies the axial force to stepped collar 542 in response to a user's activation of controls located at workstation 14. The structure applies the axial force to the stepped collar 542 to cause engagement structure 386 to disengage from the guide wire. Next, cover 384 is moved from the closed position to the open position allowing the user to access guide wire channel 390 to either remove or install the guide wire. In one embodiment, cassette 300 and/or motor drive base 302 includes motors or other actuators that cause the covers of cassette 300 to open in response to a user's activation of controls at workstation 14.

Figure 26:
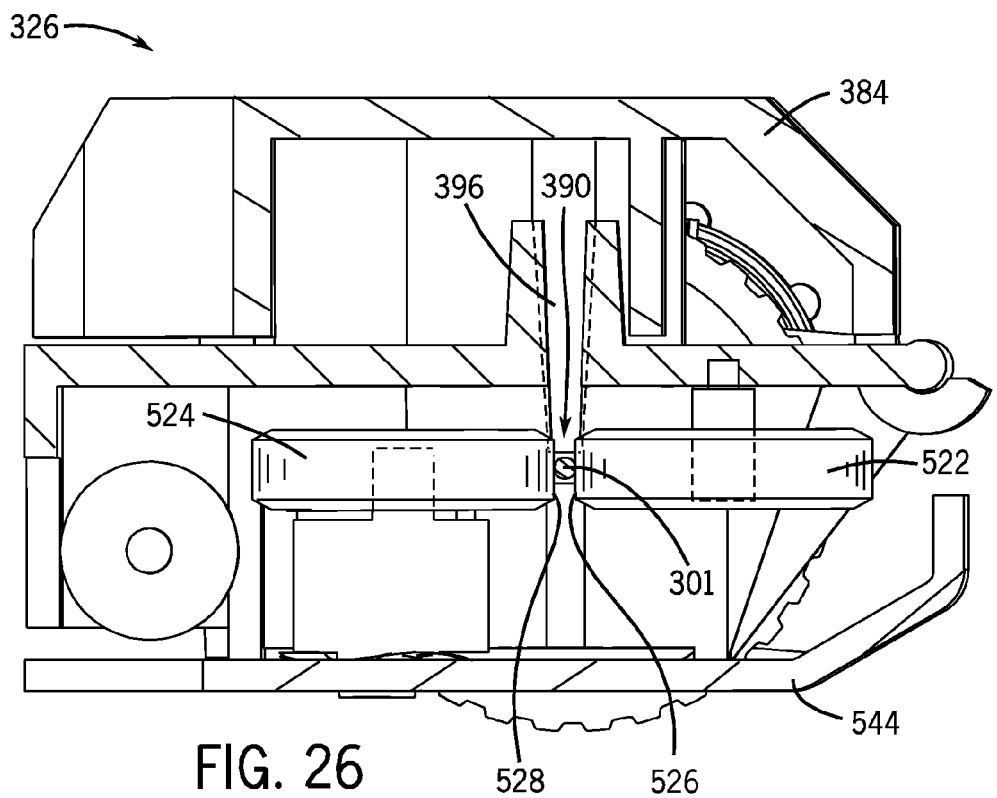
FIG. 26 is a sectional view of the rotational drive assembly taken generally along line 26-26 in FIG. 18.

FIG. 26 shows a cross-sectional view of rotational drive assembly 326 as indicated by the corresponding sectional line in FIG. 18. FIG. 26 depicts guide wire 301 within guide wire channel 390. As shown, in FIG. 26 when cover 384 is in the closed position, tab 396 rests over guide wire channel 390. As shown in FIG. 26, tab 396 helps hold guide wire 301 in guide wire channel 390 by restricting movement of guide wire 301 in a direction perpendicular to the plane defined by base plate 544 (this direction of restriction is the vertical direction in the orientation of FIG. 26). Guide wire 301 is engaged on one side by engagement surface 526 of fixed wheel 522 and on the other side by engagement surface 528 of engagement wheel 524.

Figure 27:
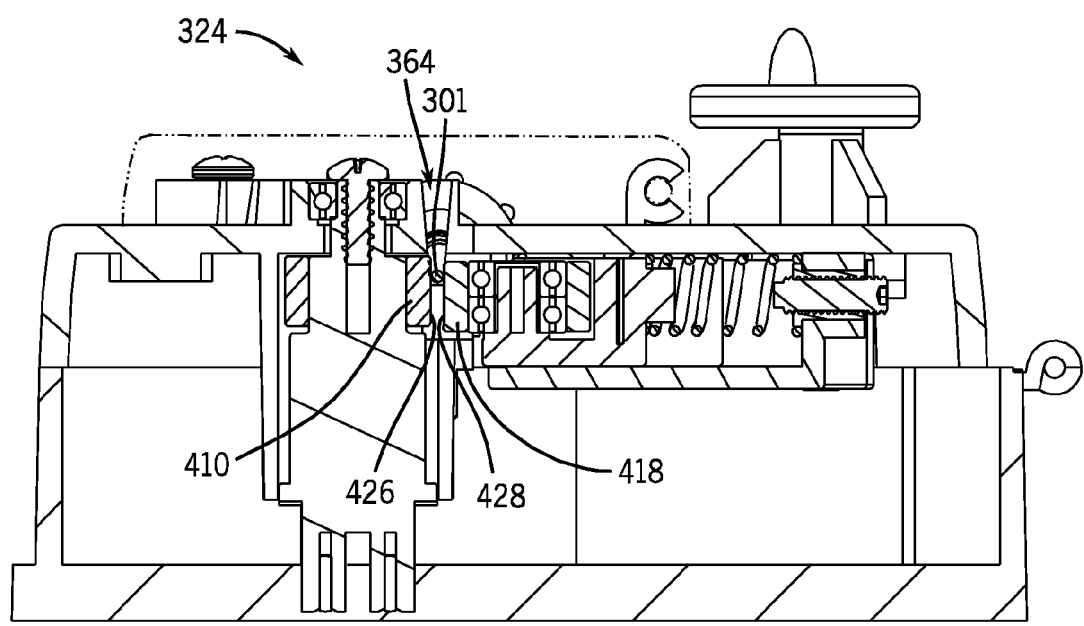
FIG. 27 is a sectional view of the axial drive assembly taken generally along line 27-27 in FIG. 18.

FIG. 27 shows a cross-sectional view of axial drive assembly 324 as indicated by the corresponding sectional line in FIG. 18. FIG. 27 depicts guide wire 301 within channel 364. Guide wire 301 is engaged on one side by engagement surface 426 of drive wheel 410 and on the other side by engagement surface 428 of roller 418.

Under certain circumstances, it may be desirable to disconnect rotational drive assembly 326 from cassette 300. Referring to FIGS. 28A-28C, cassette 300 may be configured to allow rotational drive assembly 326 (shown schematically by broken lines in FIGS. 28A-28C) to be disconnected from cassette 300. In one such embodiment, cassette 300 includes journal 388, and rotational drive mechanism 380 is rotatably coupled to journal 388. In this embodiment, journal 388 is releasably coupled to housing 316 such that both journal 388 and rotational drive mechanism 380 may be removed from housing 316 without removing the guide wire from the patient and/or without removing cassette 300 from base 302. In one such embodiment, following release of journal 388 from housing 316, the user may remove (e.g., pull, slide, etc.) both journal 388 and rotational drive mechanism 380 over the proximal end of the guide wire.

In one embodiment, journal 388 includes a slot 552, and base plate 318 includes a release button 554. Release button 554 is coupled to ramp 556, and ramp 556 includes wedge-shaped end 558. As shown in FIG. 28A, wedge-shaped end 558 passes through slot 552 to couple journal 388 to base plate 318. When a downward force is applied to release button 554, wedge-shaped end 558 is allowed to disengage from slot 552 allowing rotational drive assembly 326 and journal 388 to disconnect from base plate 318.

Next, rotational drive assembly 326 is disengaged from guide wire 301. As discussed above, regarding FIGS. 24 and 25, by applying an axial force to stepped collar 542, engagement structure 386 disengages from the guide wire. Once engagement structure 386 is disengaged from guide wire 301, the rotational drive assembly 326 may be moved over the proximal end of the guide wire while the guide wire slides freely though guide wire channel 390. Removal of rotational drive assembly 326 from cassette 300 may be necessary if, for example, bedside system 12 loses power preventing motor drive base 302 from placing rotational drive assembly into the "loading" configuration. In this case, removal of rotational drive assembly 326 allows the user to either remove the guide wire and working catheter from the patient manually or to complete the procedure manually.

In one embodiment, cassette 300 is a single-use or disposable cassette that includes a use restriction element that acts to functionally disable the cassette from being used for more than one catheterization procedure. In one embodiment, the use restriction element is a frangible piece located within one or more of the capstan sockets that prevents cassette 300 from being remounted onto the capstans of motor drive base 302 after it has been removed. In another embodiment, the use restriction element is an RFID tag that communicates with an RFID receiver indicating whether cassette 300 has previously been used. In another embodiment, the use restriction element includes a bar code associated with cassette 300 that must be scanned prior to use. If the bar code scanned is associated with a cassette that has already been used, reuse of the cassette is prevented.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Any of the features, elements, or components of any of the exemplary embodiments discussed above may be used alone or in combination with any of the features, elements, or components of any of the other embodiments discussed above. It is to be understood that the forms of the invention shown and described herein are to be taken as presently preferred embodiments. Elements and materials may be substituted for those illustrated and described herein, parts and processes may be reversed, and certain features of the invention may be utilized independently, all as would be apparent to one skilled in the art having the benefit of this description of the invention. Changes may be made in the elements described herein without departing form the spirit and scope of the invention as described in the following claims.

What is claimed is:

1. A robotic catheter system, the system comprising:
   a housing;
   a drive assembly coupled to the housing and configured to impart movement to a guide wire; and
   a release structure permitting the drive assembly to be decoupled and removed from the housing without removing the guide wire from a patient;
   wherein the drive assembly engages the guide wire intermediate a proximal end and a distal end of the guide wire.

2. The robotic catheter system of claim 1, wherein the drive assembly is removable over the proximal end of the guide wire following decoupling from the housing.

3. The robotic catheter system of claim 1, wherein the drive assembly is a rotational drive assembly and includes a rotational drive mechanism to releasably engage and rotate the guide wire about the longitudinal axis of the guide wire.

4. The robotic catheter system of claim 3, further comprising a disengagement mechanism permitting the rotational drive mechanism to be manually disengaged from the guide wire allowing the rotational drive assembly to be removed over the proximal end of the guide wire.

5. The robotic catheter system of claim 3, further comprising a journal removably coupled to the housing and coupled to the rotational drive mechanism such that the rotational drive assembly is permitted to rotate relative to the journal.

6. The robotic catheter system of claim 5, wherein the release structure engages the journal to couple the drive assembly to the housing.

7. The robotic catheter system of claim 6, wherein the release structure is moveable between a first position and a second position, and further wherein the release structure is moved to the second position to permit the drive assembly to be decoupled from the housing.

8. The robotic catheter system of claim 5, wherein the housing includes a base plate having a projection that engages a slot in the journal to couple the drive assembly to the housing, and further wherein the release structure includes a button that causes the projection to disengage from the slot when the button is pressed.

9. The robotic catheter system of claim 8, wherein the journal includes a first portion and a second portion, the first portion positioned generally perpendicular to the second portion, the first portion is in contact with the base plate of the housing when the drive assembly is coupled to the housing, the slot positioned in the first portion.

10. The robotic catheter system of claim 3, further comprising an axial drive assembly, the axial drive assembly including an axial drive mechanism to releasably engage and drive the catheter device along a longitudinal axis of the guide wire wherein the axial drive assembly is located in front of the rotational drive assembly.

11. The robotic catheter system of claim 1, wherein the housing, the drive assembly, and the release mechanism are part of a cassette configured to be mounted to a base.

12. The robotic catheter system of claim 11, wherein the cassette is a disposable cassette having a use restriction element for functionally disabling the cassette from being used for a second procedure.

13. A cassette for use with a robotic catheter system, the cassette comprising:
    a housing;
    an rotational drive assembly coupled to the housing configured to impart rotational movement to a guide wire;
    a journal removably coupled to the housing and coupled to the rotational drive mechanism such that the rotational drive assembly is permitted to rotate relative to the journal; and
    a mechanical release structure releasably engaging the journal allowing the journal to be decoupled from the housing and permitting the rotational drive assembly to be removed from the housing without removing the guide wire from a patient;
    wherein the housing is removably coupled to a base a having a motor located therein, the motor operatively coupled to the rotational drive assembly.

14. The cassette of claim 13, wherein the mechanical release structure is moveable between a first position and a second position, and further wherein the mechanical release structure is moved to the second position to allow the rotational drive assembly to be decoupled from the housing.

15. The cassette of claim 13, wherein the rotational drive assembly includes a rotational drive mechanism to releasably engage and rotate the guide wire about the longitudinal axis of the guide wire.

16. The cassette of claim 15, wherein the mechanical release structure includes a projection that releasably engages a slot in the journal to couple the journal to the housing.

17. The cassette of claim 16, wherein the housing includes a base plate, and further wherein the journal includes a first portion and a second portion, the first portion positioned generally perpendicular to the second portion, the first portion is in contact with the base plate of the housing when the drive assembly is coupled to the housing, the slot positioned in the first portion.

18. The cassette of claim 13, wherein the rotational drive assembly is removable over the proximal end of the guide wire following decoupling from the housing by moving the rotational drive assembly away from the axial drive assembly.

19. A cassette for use with a robotic catheter system configured to couple to a base, the cassette comprising:

a housing having a base plate;

a first axial drive mechanism supported by the housing to releasably engage and drive a guide wire along a longitudinal axis of the guide wire;

a rotational drive mechanism supported by the housing to rotate the guide wire about its longitudinal axis;

a journal coupled to the rotational drive mechanism and removably coupled to the housing, the journal including a first portion, a second portion, and a slot positioned in the first portion, the first portion positioned generally perpendicular to the second portion, the first portion in contact with and generally parallel to the base plate of the housing when the rotational drive mechanism is coupled to the housing;

a projection extending from the base plate that releasably engages the slot in the journal to couple the journal to the housing, and a button that causes the projection to disengage from the slot when the button is pressed allowing the journal to be decoupled from the housing allowing the rotational drive mechanism to be moved over the proximal end of the guide wire after the journal is decoupled from the housing;

wherein the base includes motor operatively engaged with the rotational drive mechanism to rotate the guide wire.

* * * * *